US006638981B2

(12) United States Patent
Williams et al.

(10) Patent No.: US 6,638,981 B2
(45) Date of Patent: Oct. 28, 2003

(54) TOPICAL COMPOSITIONS AND METHODS FOR TREATING PAIN

(75) Inventors: Robert O. Williams, Austin, TX (US); Feng Zhang, Austin, TX (US)

(73) Assignee: EpiCept Corporation, Englewood Cliffs, NJ (US)

( * ) Notice: Subject to any disclaimer, the term of this patent is extended or adjusted under 35 U.S.C. 154(b) by 0 days.

(21) Appl. No.: 09/931,293

(22) Filed: Aug. 17, 2001

(65) Prior Publication Data

US 2003/0082214 A1 May 1, 2003

(51) Int. Cl.$^7$ .............................................. A61K 31/135
(52) U.S. Cl. .................... 514/656; 514/646; 514/887; 514/817; 514/938; 424/448
(58) Field of Search .......................... 424/401; 514/938, 514/646, 656, 817

(56) References Cited

U.S. PATENT DOCUMENTS

| | | | |
|---|---|---|---|
| 4,615,699 A | 10/1986 | Gale et al. ............... | 604/897 |
| 4,751,087 A | 6/1988 | Wick ....................... | 424/449 |
| 4,755,535 A | 7/1988 | Minaskanian et al. ..... | 514/947 |
| 4,801,586 A | 1/1989 | Minaskanian et al. ..... | 514/212 |
| 4,808,414 A | 2/1989 | Peck et al. ............... | 424/449 |
| 4,920,101 A | 4/1990 | Minaskanian et al. ..... | 514/24 |
| 4,989,607 A | 2/1991 | Keusch et al. ............ | 128/640 |
| 5,635,204 A | 6/1997 | Gevirtz et al. ............ | 424/449 |
| 5,646,151 A | 7/1997 | Kruse et al. .............. | 514/255 |
| 5,648,396 A | 7/1997 | Young et al. ............. | 514/651 |
| 5,667,773 A | 9/1997 | Farrar et al. ............. | 424/78.05 |
| 5,688,955 A | 11/1997 | Kruse et al. .............. | 546/276.4 |
| 5,708,168 A | 1/1998 | Keana et al. ............. | 540/520 |
| 5,744,458 A | 4/1998 | Kruse et al. .............. | 514/91 |
| 5,760,023 A | 6/1998 | Farrar et al. ............. | 514/150 |
| 5,763,445 A | 6/1998 | Kruse et al. .............. | 514/255 |
| 5,783,700 A | 7/1998 | Nichols et al. ........... | 546/162 |
| 5,798,093 A | 8/1998 | Farrar et al. ............. | 424/45 |
| 5,811,078 A | 9/1998 | Maycock et al. .......... | 424/45 |
| 5,817,699 A | 10/1998 | Flores et al. ............. | 514/647 |
| 5,834,465 A | 11/1998 | Olney ..................... | 514/226.2 |
| 5,849,762 A | 12/1998 | Farrar et al. ............. | 414/327 |
| 5,863,916 A | 1/1999 | Cai et al. ................. | 514/249 |
| 5,869,521 A | 2/1999 | Farrar et al. ............. | 514/422 |
| 5,888,494 A | 3/1999 | Farrar et al. ............. | 424/78.05 |
| 5,914,403 A | 6/1999 | Nichols et al. ........... | 546/162 |
| 5,922,340 A | 7/1999 | Berde et al. .............. | 424/426 |
| 5,948,389 A | 9/1999 | Stein ...................... | 424/45 |
| 5,962,477 A | 10/1999 | Mak ....................... | 514/327 |
| 5,981,513 A | 11/1999 | Kruse et al. .............. | 514/91 |
| 5,985,586 A | 11/1999 | Daggett et al. ........... | 435/7.21 |
| 6,004,964 A | 12/1999 | Farrar et al. ............. | 514/255 |
| 6,017,961 A | 1/2000 | Flores et al. ............. | 514/561 |
| 6,025,369 A | 2/2000 | Rosenquist et al. ....... | 514/311 |
| 6,096,771 A | 8/2000 | Kojima et al. ............ | 514/379 |
| 6,117,855 A | 9/2000 | Carlson et al. ........... | 514/90 |
| 6,133,282 A | 10/2000 | Horvath et al. ........... | 514/292 |
| 6,172,097 B1 | 1/2001 | Cordi et al. .............. | 514/396 |
| 6,174,192 B1 | 1/2001 | Watanabe et al. .......... | 439/377 |
| 6,191,131 B1 | 2/2001 | He et al. .................. | 514/246 |
| 6,191,165 B1 | 2/2001 | Ognyanov et al. ........ | 514/523 |
| 6,197,830 B1 | 3/2001 | Frome ..................... | 514/654 |
| 6,211,171 B1 | 4/2001 | Sawynok et al. ......... | 514/211.13 |
| 6,218,391 B1 | 4/2001 | Arvanitis et al. ......... | 514/242 |
| 6,225,324 B1 | 5/2001 | Poss et al. ................ | 514/316 |
| 6,239,194 B1 | 5/2001 | Standke et al. ........... | 523/200 |
| 6,242,448 B1 | 6/2001 | Kelly et al. .............. | 514/254.02 |
| 6,245,781 B1 | 6/2001 | Upadhyay et al. ........ | 514/321 |
| 6,251,903 B1 | 6/2001 | Cai et al. ................. | 514/249 |
| 6,251,948 B1 | 6/2001 | Weber et al. ............. | 514/634 |
| 6,255,302 B1 | 7/2001 | Kelly et al. .............. | 514/217.05 |
| 6,387,957 B1 | 5/2002 | Frome ..................... | 514/647 |
| 6,461,600 B1 * | 10/2002 | Ford ....................... | 424/78.02 |

FOREIGN PATENT DOCUMENTS

| | | |
|---|---|---|
| EP | 0 107 376 A1 | 5/1984 |
| EP | 0 577 394 A1 | 1/1994 |
| WO | WO 93/10163 | 5/1993 |
| WO | WO 94/13643 | 6/1994 |
| WO | WO 94/13644 | 6/1994 |
| WO | WO 94/13661 | 6/1994 |
| WO | WO 94/13676 | 6/1994 |
| WO | WO 94/13677 | 6/1994 |
| WO | WO 95/16679 | 6/1995 |
| WO | WO 95/18124 | 6/1995 |
| WO | WO 95/23798 | 9/1995 |

OTHER PUBLICATIONS

Skin Care and Cosmetic Ingredients Dictionary, p. 243 (1994).*

"Handbook of Pharmaceutical Excipients," Edited by Arthur H. Kibbe, Ph.D., *Am. Pharm. Assoc.*, 3:292–294, 2000.

J. Sawynok et al., "Peripheral Antinociceptive Action of Amitriptyline in the Rat Formalin Test: Involvement of Adenosine," *Pain*, 80:45–55, 1999.

J. Sawynok et al., "Peripheral Antinociceptive Actions of Desipramine and Fluoxetine in an Inflammatory and Neuropathic Pain Test in the Rat," *Pain*, 82:149–158, 1999.

"Cardinal Manifestations and Presentations of Diseases," *Harrison's Principles of Internal Medicine*, Edited by A. Fauci et al., 14:1:53–58, 1998.

C. Stein et al., "Peripheral Morphine Analgesia", *Pain*, 71:119–121, 1997.

(List continued on next page.)

*Primary Examiner*—Jyothsna Venkat
(74) *Attorney, Agent, or Firm*—Pennie & Edmonds, LLP

(57) ABSTRACT

Topical compositions and methods for treating pain. The invention provides oil-in-water emulsions comprising an antidepressant; an NMDA-receptor antagonists; a lipophilic component; water; and a surfactant. The compositions induce a local-anesthetic effect when topically administered to intact skin thereby treating or preventing pain, for example, neuropathic pain.

9 Claims, No Drawings

OTHER PUBLICATIONS

T. Ghosh et al., Transdermal and Topical Drug Delivery Systems, "Types of Dermal Drug Delivery," *Interpharm Press, Inc.,* p. 7, 1997.

T. Ghosh et al., Transdermal and Topical Drug Delivery Systems, "Transdermal and Dermal Therapeutic Systems," *Interpharm Press, Inc.,* pp. 87–93, 1997.

T. Ghosh et al., Transdermal and Topical Drug Delivery Systems, "Transdermal and Dermal Therapeutic Systems: Current Status," *Interpharm Press, Inc.,* p. 33–112, 1997.

Goodman & Gilman's The Pharmacological Basis of Therapeutics, Edited by J. Hardman et al., "Chapter 23 Opioid Analgesics and Antagonists," 9:521–525, 1996.

Goodman & Gilman's The Pharmacological Basis of Therapeutics, Edited by J. Hardman et al., "Chapter 23 Opioid Analgesics and Antagonists," 9:529, 1996.

Gennaro, Remington: The Science and Practice of Pharmacy, "Coarse Dispersions," 19(1):289, 1995.

Wolfe et al., "Massive Dextromethorphan Ingestion and Abuse," *Am J. Emerg Med. P.,* 13:174–176, 1995.

Jia–He Li et al., "Potent, Orally Active, Competitive N–Methyl–D–aspartate (NMDA) Receptor Antagonists Are Substractes for a Neutral Amino Acid Update System in Chinese Hamster Overy Cells," *J. Med. Chem.,* 38:1955–1965, 1995.

Olney et al., "NDMA Antagonists as Neurotherapeutic Drugs, Psychotogens, Neurotoxins, and Research Tools for Studying Schizophrenia," *Neuropsychopharmacology,* 13(4):335–345, 1995.

Yoneda et al., "Differential Profiles of Binding of a Radiolabeled Agonist and Antagonist at a Glycine Recognition Domain on the N–Methyl–D–Aspartate Receptor Ionophore Complex in Rat Brain," *J. Neurochem.* 62(1):102–112, 1994.

Bigge, "Structural Requirements for the Development of Potent N–Methyl–D–Aspartic Acid (NMDA) Receptor Antagonists," *Biochem. Pharmacol. P.,* 45(8):1547–1561, 1993.

T. Ghosh et al., "Methods of Enhancement of Transdermal Drug Delivery: Part IIA, Chemical Permeation Enhancers," *Pharm. Tech.,* 17:62–90, 1993.

T. Ghosh et al., "Methods of Enhancement of Transdermal Drug Delivery: Part IIB, Chemical Permeation Enhancers," *Pharm. Tech.,* 17:68–76, 1993.

P. Leeson, "Glycine–Site N–Methyl–D–Aspartate Receptor Antagonists," *Drug Design for Neuroscience,* pp. 338–381, 1993.

Wong et al., "Norfluoxetine Enantiomers as Inhibitors of Serotonin Uptake in Rat Brain," *Neuropsychoopharmacology,* 8(4):337–344, 1993.

Albers et al., "Tolerability of Oral Dextromethorphan in Patients With a History of Brain Ischemia," *Clinical Neurpharmacology,* 15(6):509–514, 1992.

Faden et al., "Pharmacological Strategies in CNS Trauma," *TiPS,* 13:29–35, 1992.

Steinberg et al., "Dextromethorphan Alters Cerebral Blood Flow and Protects Against Cerebral Injury Following Focal Ischemia," *Neuroscience Letters,* 133:225–228, 1991.

Meldrum et al., "Excitatory Amino Acid Neurotoxicity and Neurodegenerative Disease," *TiPS,* 11:379–387, 1990.

Willetts et al., "The Behavioral Pharmacology of NMDA Receptor Antagonists," *TiPS,* 11:423–428, 1990.

"Percutaneous Absorption," edited by R. Bronaugh et al., $2^{nd}$ Ed., Contents, 1989.

Mayer et al., "Sites of Antagonist Action on N–Methyl–D–Aspartic Acid Receptors Studied Using Fluctuation Analysis and a Rapid Perfusion Technique," *Journal of Neurophysiology,* 60(2):645–663, 1988.

Thurkauf et al., "Synthesis, Absolute Configuration, and Molecular Modeling Study of Etoxadrol, a Potent Phencyclidine–Like Agonist," *J. Med. Chem.,* 31:2257–2263, 1988.

G. Eccleston, "Emulsions," Encyclopedia of Pharmaceutical Technology, edited by J. Swarbrick et al., 5:137–189, 1988.

J. Dohner, "Development of Processes and Equipment for Rate–Controlled Transdermal Therapeutic Systems," Transdermal Controlled Systemic Medications, edited by Y. Chien, pp 349–364,1987.

H. Wolff et al., "Development of Processes and Technology for Adhesive–Type Transdermal Therapeutic Systems," Transdermal Controlled Systemic Medications, edited by Y. Chien, pp 365–378, 1987.

D. Bova et al., "Product Development and Technology Transfer for Transdermal Therapeutic Systems," Transdermal Controlled Systemic Medications, edited by Y. Chien, pp 379–396, 1987.

A. Jacobson et al., "Enantiomeric and Diastereomeric Dioxadrols: Behavioral, Biochemical and Chemical Determination of the Configuration Necessary for Phencyclidine–Like Properties," *J. Pharmacol. Exp. Ther. P.,* 243(1):110–117, 1987.

M. Rogawski, "Therapeutic Potential of Excitatory Amino Acid Antagonists: Channel Blockers and 2,3–benzodiazepines," *TiPS,* 14:325–331, 1993.

Grimwood et al., "Characterization of the Binding of [$^3$H] L–689,560, An Antagonist for the Glycine Site on the N–Methyl–D–Aspartate Receptor, to Rat Brain Membranes," *Molecular Pharmacology,* 41:923–930, 1992.

Skolnick et al., "Monoaminergic Involvement in the Pharmacological Actions of Buspirone," *Br. J. Pharmac,* 86:637–644, 1985.

Wong et al., "A New Inhibitor of Norepinephrine Uptake Devoid of Affinity for Receptors in Rat Brain," *J. Pharm. Exp. Therap.,* 222(1):61–65, 1982.

Kinemuchi et al., "Substrate Selectivity of Type A and Type B Monoamine Oxidase in Rat Brain," *J. Neurochem.,* 35(1):109–115, 1980.

W. Griffin, "Classificationof Surface–Active Agents by HLB," *J. Soc. Cosmet. Chem.,* 311–326, 1949.

* cited by examiner

TOPICAL COMPOSITIONS AND METHODS FOR TREATING PAIN

I. FIELD OF THE INVENTION

The present invention relates to methods for treating or preventing pain via topical formulations that induce a local-anesthetic effect when applied to intact skin. The compositions comprise an antidepressant and a N-methyl-D-aspartate-receptor antagonist.

II. BACKGROUND OF THE INVENTION

Pain results from the noxious stimulation of nerve endings. Nociceptive pain is caused by noxious stimulation of nociceptors (e.g., a needle stick or skin pinch), which then transmit impulses over intact neural pathways to the spinal neurons and then to the brain. Neuropathic pain is caused by damage to neural structures, such as damage to peripheral nerve endings or nociceptors, which become extremely sensitive to stimulation and can generate impulses in the absence of stimulation (e.g., herpes zoster pain after the rash has healed). Peripheral nerve damage can lead to pathological states where there is a reduction in pain threshold (i.e., allodynia), an increased response to noxious stimuli (hyperalgesia), or an increased response duration (persistent pain). GOODMAN & GILMAN'S THE PHARMACOLOGICAL BASIS OF THERAPEUTICS 529 (Joel G. Hardman et al. eds., 9th ed. 1996); HARRISON'S PRINCIPLES OF INTERNAL MEDICINE 53–58 (Anthony S. Fauci et al. eds., 14th ed. 1998).

In contrast to pain treatment with systemic agents, pain can be treated locally by topically administering a local anesthetic directly to the painful area to block the nociceptive mechanistic pathway. Local anesthetics prevent the generation and conduction of nociceptive nerve impulses. Thus, for example, a local anesthetic can be injected intradermally (non-systemic injection within the skin) or topically applied at the pain area. Advantages of topical local-anesthetic administration over systemic administration of pain relievers include decrease or preclusion of side effects, improved patient compliance, and reversible action (i.e., the action can be reversed by removing the anesthetic from the application site). TRANSDERMAL AND TOPICAL DRUG DELIVERY SYSTEMS 33–112 (Tapash K. Ghosh et al. eds., 1997).

A variety of drug classes have local-anesthetic properties and can be administered in topical formulations. Traditional local anesthetics or sodium-channel blockers, such as lidocaine prevent the generation and conduction of nerve impulses by decreasing or preventing the large transient increase in the permeability of excitable membranes to Na+. Other agents with local-anesthetic properties include analgesics, such as non-steroidal anti-inflammatories ("NSAIDs"), see, for example, TRANSDERMAL AND TOPICAL DRUG DELIVERY SYSTEMS 87–93 (Tapash K. Ghosh et al. eds., 1997) and opioids, such as morphine. See e.g., U.S. Pat. No. 5,948,389 (issued Sept. 7, 1999); Christoph Stein & Alexander Yassouridis 71 Pain 119 (1997).

N-methyl-D-aspartate ("NMDA") receptor antagonists, such as ketamine have local-aesthetic properties and topical administration is as an effective neuropathic pain treatment. See, for example, U.S. Pat. No. 5,817,699 (issued Oct. 6, 1998). In another example, topical administration of antidepressant medications, such as amitriptyline, has been reported effective for neuropathic pain treatment. See, for example, U.S. Pat. No. 6,211,171 (issued Apr. 3, 2001); J. Sawynok et al., 82 PAIN 149 (1999). In addition, topical administration of a combination of a tricyclic antidepressant and an NMDA-receptor antagonist is reported to have excellent local-anesthetic properties when topically applied and is useful for treatment of neuropathic pain, U.S. Pat. No. 6,197,830 (issued Mar. 6, 2001).

But even though topical local-anesthetic administration to intact skin is routinely used to treat minor indications, it has not found significant use for treating more severe nociceptive and neuropathic pain because it is difficult to get significant concentrations through the skin barrier. Because of the skin's drug-permeation resistance, as little as about 1 percent and usually no more than about 15 percent of a drug in a topical formulation is bioavailable (TRANSDERMAL AND TOPICAL DRUG DELIVERY SYSTEMS 7 (Tapash K. Ghosh et al. eds., 1997)). Another problem with topical administration of pain relievers is stability of the composition. Local-anesthetics emulsion compositions are inherently unstable, and phase separation can occur during shipment and storage. Furthermore, many topical local-anesthetic compositions suffer from oxidative instability. Lecithin compositions are routinely used as bases for topical local-aesthetic compositions, but are highly oxidatively unstable (AM. PHARM. ASSOC., HANDBOOK OF PHARMACEUTICAL EXCIPIENTS 292–294, 292 (Arthur H. Kibbe ed., 3rd ed. 2000)). For example, U.S. Pat. No. 6,197,830 (issued Mar. 6, 2001) describes a lecithin-based composition for topically administering a combination of an NMDA-receptor antagonist and a tricyclic antidepressant and U.S. Pat. No. 5,817,699 (issued Oct. 6, 1998) and U.S. Pat. No. 6,017,961 (issued Jan. 25, 2000) describe topical administration of ketamine in pluronic lecithin organogel.

In sum, topical local-anesthetic administration has advantages over systemic administration of pain relievers. Unfortunately, topical local-anesthetic compositions suffer from instability and poor skin-penetration properties, which limit their use to less severe pain. What are needed are stable topical local-anesthetic compositions with good skin-penetration properties. Particularly, stable, skin-penetrating compositions comprising a combination of an antidepressant and an NMDA-receptor antagonists are needed.

Citation or identification of any reference in the Background section of this application is not an admission that such reference is prior art to the present invention.

III. SUMMARY OF THE INVENTION

The invention provides methods and topical compositions for treating or preventing pain. The compositions of the invention can be topically administered to intact skin to provide a local-anesthetic effect thereby treating or preventing pain, for example, neuropathic pain. In one embodiment, the invention provides stable, skin penetrating compositions for topical administration comprising a combination of an antidepressant and an NMDA-receptor antagonist.

In a second embodiment, the invention provides an emulsion comprising:

(a) an antidepressant or a pharmaceutically acceptable salt thereof;

(b) an NMDA-receptor antagonists or a pharmaceutically acceptable salt thereof;

(c) a lipophilic component;

(d) water; and (e) a surfactant, wherein the emulsion is an oil-in-water emulsion.

Preferably, the mean oil-droplet size is within the range of about 0.01 microns to about 100 microns, more preferably, within the range of about 0.1 microns to about 10 microns.

In another embodiment, the invention relates to a patch comprising:

(a) an antidepressant or a pharmaceutically acceptable salt thereof;

(b) an NMDA receptor antagonists or a pharmaceutically acceptable salt thereof;

(c) a lipophilic component;

(d) water; and (e) a surfactant, wherein the emulsion is an oil in water emulsion.

In still another embodiment, the invention provides a method of treating or preventing pain in a mammal comprising topically administering to the skin of a mammal in need thereof an emulsion comprising:

(a) a therapeutically effective amount of an antidepressant or a pharmaceutically acceptable salt thereof;

(b) a therapeutically effective amount of an NMDA-receptor antagonists or a pharmaceutically acceptable salt thereof;

(c) a lipophilic component;

(d) water; and (e) a surfactant, wherein the emulsion is an oil-in-water emulsion.

In still another embodiment, the invention relates to a method of inducing local anesthesia in a mammal comprising topically administering to the skin of a mammal in need thereof an emulsion comprising:

(a) a therapeutically effective amount of an antidepressant or a pharmaceutically acceptable salt thereof;

(b) a therapeutically effective amount of an NMDA-receptor antagonists or a pharmaceutically acceptable salt thereof, (c) a lipophilic component;

(d) water; and (e) a surfactant, wherein the emulsion is an oil-in-water emulsion.

The present invention may be understood more fully by reference to the following figures, detailed description and illustrative examples, which are intended to exemplify non-limiting embodiments of the invention.

IV. DEFINITIONS

As used herein, the phrase "composition of the invention" refers to an oil-in-water emulsion having a mean droplet size within the range of 0.01 microns to 100 microns comprising:

(1) a therapeutically effective amount of an antidepressant, a pharmaceutically acceptable salts thereof, a complex thereof (e.g., hydrates, solvates, and clathrates), a prodrug thereof, or any stereoisomeric forms or mixtures of stereoisomeric forms thereof (e.g., geometrical isomers, enantiomers, diastereomers, racemates, or mixtures thereof);

(2) a therapeutically effective amount of an NMDA-receptor antagonists, a pharmaceutically acceptable salts thereof, a complex thereof (e.g., hydrates, solvates, and clathrates), a prodrug thereof, or any stereoisomeric forms or mixtures of stereoisomeric forms thereof (e.g., geometrical isomers, enantiomers, diastereomers, racemates, or mixtures thereof);

(3) a lipophilic component;

(4) water; and (5) a surfactant.

As used herein, a "therapeutically effective amount" of an antidepressant or an NMDA-receptor antagonist means the amount of the antidepressant or the NMDA-receptor antagonist required in a composition of the invention to induce a local-anesthetic effect sufficient to treat or ameliorate pain in a mammal.

As used herein, the term mammal means any mammal, for example, but not limited to humans; pets, such as dogs and cats; farm mammals, such as horses, cows, pigs, and sheep; and laboratory animals, such as monkeys, guinea pigs, rats, and mice. Preferably, a "mammal" is a human.

As used herein, the term "intradermal administration" means administration of a pharmaceutical to the skin of a mammal, preferably a human, to deliver the pharmaceutical to the local tissue under and around the site of administration. Preferably, intradermal administration is effected without absorption of the pharmaceutical into the mammal's blood stream. The purpose of intradermal administration is to elicit a local affect in contrast to transdermal administration where the objective is to transfer the pharmaceutical through the skin and into the blood stream for a systemic effect.

As used herein, the term "topical administration" or "topical delivery" means intradermal administration of a pharmaceutical by administration of the pharmaceutical or a composition comprising the pharmaceutical to intact skin. For example, by rubbing a composition of the invention onto an area of intact skin or by placing an intradermal patch comprising a composition of the invention onto an area of intact skin.

The term "topical composition" means a pharmaceutical composition designed for topical administration and containing a pharmaceutical.

As used herein, the phrase "intradermally-acceptable" means any pharmaceutical, excipient or other component of a topical formulation that is safe or approved for intradermal or topical administration in mammals.

The phrase "pharmaceutically acceptable salt(s)," as used herein includes, but is not limited to, salts of acidic or basic groups that may be present in the compounds of the invention. Compounds of the invention that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate (i.e., 1,1'-methylene-bis-(2-hydroxy-3-naphthoate)). Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, the term "solvate" means a compound of the invention or a salt thereof, that further includes a stoichiometric or non-stoichiometric amount of a solvent bound by non-covalent intermolecular forces. Preferred solvents are volatile, non-toxic, and/or acceptable for topical administration to humans.

As used herein, the term "hydrate" means a compound of the invention or a salt thereof, that further includes a stoichiometric or non-stoichiometric amount of water bound by non-covalent intermolecular forces.

The term "clathrate" means a compound of the invention or a salt thereof in the form of a crystal lattice that contains spaces (e.g., channels) that have a guest molecule (e.g., a solvent or water) trapped within.

The term "prodrug" refers to a compound that, following administration in a mammal, converts, via a biotransformation, into an antidepressant or an NMDA-receptor antagonist in vivo. Prodrugs can be synthesized using well-known methods, such as those described by 1 BURGER'S MEDICINAL CHEMISTRY AND DRUG DISCOVERY, 172–178, 949–982 (Manfred E. Wolff ed., 5th ed. 1995).

As used herein, an "emulsion" means a dispersed system containing at lease two immiscible phases (a lipophilic phase and a hydrophilic or aqueous phase), wherein one immiscible phase is dispersed within the other in the form of droplets. Emulsions are thermodynamically unstable as a result of excess free energy associated with the surface of the droplet. A stable emulsion must contain at least three components, i.e., a dispersion medium, a dispersed phase, and an emulsifying agent. As used herein, a "oil-in-water type emulsion" is a stable emulsion in which the aqueous phase is the dispersion medium and the lipophilic component is the dispersed phase. Several tests are available to determine whether an emulsion is an oil-in-water type emulsion or a water-in-oil type emulsion: for example, the dilution test, the conductivity test, and the dye solubility test, which tests are described in 1 REMINGTON: THE SCIENCE AND PRACTICE OF PHARMACY 282–291 (Alfonso R. Gennaro ed., 19th ed. 1995), hereby expressly incorporated herein by reference.

V. DETAILED DESCRIPTION OF THE INVENTION

The compositions of the invention comprise an antidepressant and an NMDA-receptor antagonist in a colloidal dispersion (emulsion). The colloidal dispersion comprises an aqueous phase, a lipophilic phase, and a surfactant system, wherein the lipophilic phase is dispersed within the aqueous phase (oil-in-water emulsion) and the mean-droplet size is within the range of about 0.01 microns to about 100 microns, preferably about 0.1 microns to 10 about microns. In a preferred embodiment, the compositions of the invention further comprise a stiffening agent and a hydrophobic surfactant. When topically administered to a mammal, the compositions of the invention can deliver a combination of an antidepressant and an NMDA-receptor antagonist through intact skin at a high flux rate to induce local anesthesia and thereby treat, ameliorate, or prevent neuropathic pain. Furthermore, the compositions of the invention are stable both physically (resists coalescing of droplets and Ostwald ripening) and chemically stable (e.g., resist oxidation) and impart a soothing feeling when administered.

A. Pain Indications

The compositions and methods of the invention can be used to treat or prevent any indication resulting from noxious stimulation of peripheral nociceptors. The compositions and methods of the invention are effective to induce local anesthesia and to treat neuropathic pain. As used herein the term "neuropathic pain" refers to neuropathic-pain syndromes, that is, pain due to lesions or dysfunction in the nervous system. The compositions and methods of the invention can be used to treat or prevent pain related to or induced by the following diseases, trauma, or conditions: general neuropathic conditions, such as peripheral neuropathy, phantom pain, reflex-sympathetic dystrophy, causalgia, syringomyelia, and painful scar; specific neuralgias at any location of the body; back pain; diabetic neuropathy; alcoholic neuropathy; metabolic neuropathy; inflammatory neuropathy; chemotherapy-induced neuropathy, herpetic neuralgias; traumatic odontalgia; endodontic odontalgia; thoracic-outlet syndrome; cervical, thoracic, or lumbar radiculopathies with nerve compression; cancer with nerve invasion; traumatic-avulsion injuries; mastectomy, thoracotomy pain; spinal-cord-injury; stroke; abdominal-cutaneous nerve entrapments; tumors of neural tissues; arachnoiditis; stump pain; fibromyalgia; regional sprains or strains; myofascial pain; psoriatic arthropathy; polyarteritis nodosa; osteomyelitis; bums involving nerve damage; AIDS-related pain syndromes; connective tissue disorders, such as systemic lupus erythematosis, systemic sclerosis, polymyositis, and dermatomyositis; and inflammatory conditions, such as acute inflammation (e.g. trauma, surgery and infection) or chronic inflammation (e.g., arthritis and gout).

B. Antidepressants

The term "antidepressant" means any compound or composition known or to be discovered that, when tested according to standard in vivo or in vitro assays, displays receptor-binding properties or other mechanistic properties associated with the clinically approved antidepressants or any compound or composition known or to be discovered that has demonstrated clinical efficacy in treating depression in mammals including those compounds and compositions that have been approved for treating depression in humans.

Classes of antidepressant agents include norepinephrine-reuptake inhibitors (NRIs"), selective-serotonin-reuptake inhibitors (SSRIs), monoamine-oxidase inhibitors (MAOIs), serotonin-and-noradrenaline-reuptake inhibitors ("SNFIs); corticotropin-releasing factor (CRF) antagonists, α-adrenoreceptor antagonists; NK1-receptor antagonists, 5-HT$_{1A}$-receptor agonist, antagonists, and partial agonists, atypical antidepressants, and other antidepressants.

An antidepressant can contain one or more chiral centers and/or double bonds and, therefore, exist as stereoisomers, such as double-bond isomers (i.e., geometric isomers), enantiomers, or diastereomers. As used herein, the term "antidepressant" encompass all such enantiomers and stereoisomers, that is, both the stereomerically-pure form (e.g., geometrically pure, enantiomerically pure, or diastereomerically pure) and enantiomeric and stereoisomeric mixtures, e.g., racemates. The term "antidepressant" further encompasses all pharmaceutically acceptable salts, all complexes (e.g., hydrates, solvates, and clathrates), and all prodrugs of antidepressants.

Notably, the methods of the invention involve topical administration, thus "antidepressants" unsuitable for systemic administration in mammals, because of toxicity or otherwise, may still be suitable for topical administration in combination with an NMDA-receptor antagonist according to the compositions and methods of the invention. Antidepressants suitable for use in the invention can be identified by testing antidepressant compounds for local-anesthetic and peripheral antinociceptive properties according to standard pain models. See, for example, J. Sawynok et al., 82 PAIN 149 (1999); J. Sawynok et al., 80 PAIN 45 (1999), both of which citations are hereby expressly incorporated by reference herein.

Preferably an antidepressant is a norepinephrine-reuptake inhibitor, more preferably, a tricyclic antidepressant, most preferably, amitriptyline, even more preferably amitriptyline hydrochloride.

1. Norepinephrine-reuptake Inhibitors

The term "antidepressant" as used herein includes compounds that when administered systemically in a mammal, inhibit norepinephrine-reuptake ("norepinephrine-reuptake inhibitors") or that when tested according to standard in vivo or in vitro assays, display receptor-binding properties or other mechanistic properties associated with norepinephrine-reuptake inhibitors. One of skill in the art can readily identify norepinephrine-reuptake inhibitors by in vivo and in vitro assays. For example, norepinephrine-reuptake inhibitors can be identified by adapting the in vitro test method described by Wong et al., 61 J. PHARM. EXP. THERAP. 222 (1982); P. Skolnick et al., 86 BR. J. PHARMACOLOGY 637–644 (1985), hereby expressly incorporated herein by reference. Examples of norepinephrine-reuptake inhibitors include, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and pharmaceutically acceptable salts thereof. Examples of other norepinephrine-reuptake inhibitors include the tricyclic compounds encompassed by the generic formula disclosed in U.S. Pat. No. 6,211,171 (issued Apr. 30, 2001) column 9, lines 30–65 and pharmaceutically acceptable salts thereof, hereby expressly incorporated herein by reference.

2. Serotonin-reuptake Inhibitors

The term "antidepressants" also includes compounds that inhibit reuptake of serotonin ("serotonin reuptake inhibitors") when systemically administered in mammals or that when tested according to standard in vivo or in vitro assays, display receptor-binding properties or other mechanistic properties associated with serotonin-reuptake inhibitors. One of skill in the art can readily identify serotonin-reuptake inhibitors. For example, serotonin-reuptake inhibitors can be identified by adapting the in vitro test methods described in Wong, et al., 8 NEUROPSYCHOPHARMACOLOGY 337 (1993); U.S. Pat. No. 6,225,324 (issued May 1, 2001), column 20, lines 20–67; and U.S. Pat. No. 5,648,396 (issued Jul. 15, 1997) column 15, line 33 through column 16, line 44, hereby expressly incorporated herein by reference. Examples of serotonin-reuptake inhibitors include, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine, and pharmaceutically acceptable salts thereof.

3. Monoamine-oxidase Inhibitors

The term "antidepressant" as used herein includes compounds that when administered systemically in a mammal, act as monoamine-oxidase inhibitors ("MAOIs") or that when tested according to standard in vivo or in vitro assays, inhibit monoamine oxidase. One of skill in the art can readily identify MAOIs by in vivo and in vitro assays. For example, MAOIs can be identified by adapting the monoamine-oxidase inhibitory assay described in 12 Biochem. Pharmacol. 1439 (1963) and Kinemuchi et al., 35 J. NEUROCHEM. 109 (1980); U.S. Pat. No. 6,096,771 (issued Aug. 1, 2000), all of which citations are hereby expressly incorporated herein by reference.

Examples of non-selective MAO inhibitors include, but are not limited to, amiflamine, vanoxerine (boxeprazine), AGN 2253 (Nicholas Kiwi), iproniazid, isocarboxazid, M-3-PPC (Draxis), nialamid, phenelzine, pargyline, and tranylcypromine and pharmaceutically acceptable salts thereof.

Examples selective MAO A inhibitors include, but are not limited to, clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41–1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671 and pharmaceutically acceptable salts thereof.

Other MAO A inhibitors include budipine, caroxazone, D-1711 (Biocodex), fezolamine, FLA-334 (RAN-113) (Astra), FLA-289 (FLA-299, FLA-365, FLA-384, FLA-463, FLA-727) (Astra), K-1566 (Pharmacia Upjohn, Farmitalia), K-1829 (Pharmacia Upjohn, Farmitalia), metralindole, MPCPAM (Yissum), PharmaProjects 227 (Syntex/Roche), PharmaProjects 2806 (Fournier), PharmaProjects 1122, PharmaProjects 3311 (Roche), PharmaProjects 4433 (Roche), RS-2232 (Sankyo), and UP-614-04 (Bristol-Myers) and pharmaceutically acceptable salts thereof.

Other MAO inhibitors include bifemelane, brofaromide, hypericin, iproclozide, medifoxamine, nialamide, octamoxin, phenoxypropaazine, pivalyl benzhydrazine, prodipine, selegiline, and benmoxine and pharmaceutically acceptable salts thereof.

4. Serotonin- and Noradrenalin-Reuptake Inhibitors

The term "antidepressant" as used herein includes compounds that when administered systemically in a mammal, act as serotonin- and noradrenaline-reuptake inhibitors ("SNRIs") or that when tested according to standard in vivo or in vitro assays, display receptor-binding properties or other mechanistic properties associated with serotonin- and noradrenalin-reuptake inhibitors. One of skill in the art can readily identify SNRIs by in vivo and in vitro assays. For example, SNRIs can be identified by adapting the in vitro test method described in U.S. Pat. No. 6,172,097 (issued Jan. 9, 2001), hereby expressly incorporated herein by reference. Examples of SNRIs include, but are not limited to, mirtazapine, and venlafaxine and pharmaceutically acceptable salts thereof 5. Corticotropin-releasing-factor Antagonists The term "antidepressant" as used herein includes compounds that when administered systemically in a mammal, act as corticotropin-releasing factor antagonists ("CRF antagonists") or that when tested according to standard in vivo or in vitro assays, display receptor-binding properties or other mechanistic properties associated with CRF antagonists. One of skill in the art can readily identify CRF antagonists by in vivo and in vitro assays. For example, CRF antagonists can be identified by adapting the in vitro test method described in U.S. Pat. No. 6,218,391 (issued Apr. 17, 2001), hereby expressly incorporated herein by reference.

Examples of CRF antagonists include, but are not limited to, those described in U.S. Pat. No. 6,191,131 (issued Feb. 20, 2001); U.S. Pat. No. 6,174,192 (issued Jan. 16, 2001); U.S. Pat. No. 6,133,282 (issued Oct. 17, 2000); PCT Patent Application Publication Nos. WO 94/13643, WO 94/13644, WO 94/13661, WO 94/13676 and WO 94/13677, and pharmaceutically acceptable salts thereof, all of which patents and publications are hereby expressly incorporated herein by reference.

6. α-Adrenoreceptor Antagonists

The term "antidepressant" as used herein includes compounds that when administered systemically in a mammal, act as α-adrenoreceptor antagonists or that when tested according to standard in vivo or in vitro assays, act as α-adrenoreceptor antagonists. One of skill in the art can readily identify α-adrenoreceptor antagonists by in vivo and in vitro assays. For example, α-adrenoreceptor antagonists can be identified by adapting the in vitro test method described in U.S. Pat. No. 6,150,389 (issued Nov. 21, 2000), hereby expressly incorporated herein by reference.

Examples of α-adrenoreceptor antagonists include, but are not limited to, phentolamine and those described in U.S. Pat. No. 6,150,389 and pharmaceutically acceptable salts thereof.

7. NK1-Receptor Antagonists

The term "antidepressant" as used herein includes compounds that when administered systemically in a mammal, act as NK1-receptor antagonists (Neurokinin 1 substance P receptor antagonists) or that when tested according to standard in vivo or in vitro assays, act as NK1-receptor antagonists. One of skill in the art can readily identify NK1-receptor antagonists by in vivo and in vitro assays. For example, NK1-receptor antagonists can be identified by adapting the NK1-receptor-binding assay described in U.S. Pat. No. 6,117,855 (issued Sep. 12, 2000), hereby expressly incorporated herein by reference.

Examples of NK1-receptor antagonists include, but are not limited to, those described in PCT Patent Application Publication Nos. WO 95/16679, WO 95/18124, WO 95/23798, and European Patent Specification No. 0 577 394 and pharmaceutically acceptable salts thereof, all of which publications and patent are hereby expressly incorporated herein by reference.

8. 5-$HT_{1A}$-receptor Agonist, Antagonists, and Partial Agonists

The term "antidepressant" as used herein includes compounds that when administered systemically in a mammal, act as 5-$HT_{1A}$-receptor agonist, antagonists, and partial agonists ("5-$HT_{1A}$ agents") or that when tested according to standard in vivo or in vitro assays, act as 5-$HT_{1A}$-receptor agonist, antagonists, and partial agonists. One of skill in the art can readily identify 5-$HT_{1A}$ agents by in vivo and in vitro assays. For example, 5-$HT_{1A}$ agents can be identified by adapting the 5-$HT_{1A}$ receptor binding assays described in U.S. Pat. No. 6,255,302 (issued Jul. 3, 2001) or U.S. Pat. No. 6,239,194 (issued May 29, 2001), which patents are hereby expressly incorporated herein by reference.

Examples of 5-$HT_{1A}$ agents include, but are not limited to, buspirone, flesinoxan, gepirone, and ipsapirone, and pharmaceutically acceptable salts thereof and those disclosed in U.S. Pat. Nos. 6,255,302; 6,245,781 (issued Jun. 12, 2001); and U.S. Pat. No. 6,242,448 (issued Jun. 5, 2001). An example of a compound with 5-$HT_{1A}$ receptor antagonist/partial agonist activity is pindolol.

9. Atypical Antidepressants

The term "antidepressants" also includes atypical antidepressants. Examples of atypical antidepressants include, but are not limited to bupropion, dimethazan, fencamine, fenpentadiol, levophacetoperance, metralindone, mianserin, cotinine, rolicyprine, rolipram, nefopam, lithium, trazodone, viloxazine, and sibutramine and pharmaceutically acceptable salts thereof.

10. Other Antidepressants

The term "antidepressants" also includes a wide variety of other drugs that are thought to have antidepressant activity including, but not limited to, nomifensine, oxitriptan, oxypertine, thiazesim, adrafinil, benactyzine, butacetin, dioxadrol, febarbamate, hematoporphyrin, minaprine, piberaline, pyrisuccideanol, roxindole, rubidium chloride, sulpride, thozalinone, tofenacin, l-tryptophan, alaproclate, amitriptyline-chlordiazepoxide combination, atipamezole, azamianserin, bazinaprine, befuraline, binodaline, bipenamol, cericlamine, cianopramine, cimoxatone, clemeprol, clovoxamine, dazepinil, deanol, enefexine, estazolam, fezolamine, fluotracen, idazoxan, levoprotiline, litoxetine, montirelin, nebracetam, norfluoxetine, orotirelin, oxaflozane, pinazepam, pirlindone, setiptiline, sulbutiamine, sulpiride, teniloxazine, thymoliberin, tiflucarbine, tofisopam, tomoxetine, veralipride, viqualine, zimelidine and zometapine, and pharmaceutically acceptable salts thereof, and St. John's wort herb or hypericum perforatum, or extracts thereof.

11. Concentration of Antidepressant in Compositions of the Invention

The amount of antidepressant in compositions of the invention will vary according to the type and identity of the antidepressant, the concentration and identity of the NMDA-receptor antagonist, and the painful indiction treated. Dosages and concentrations for a particular antidepressants can be optimized according to routine experiments using well-known pain models, for example, those described in J. Sawynok et al., 82 PAIN 149 (1999) and J. Sawynok et al., 80 PAIN 45 (1999).

In general, the amount of antidepressant in the composition is of the invention is within the range of from about 0.1 percent to about 10 percent of the total weight of the composition, more preferably, of from about 0.5 percent to about 8 percent, still more preferably, of from about 1 percent to about 5 percent of the total weight of the composition.

C. N-Methyl-D-Aspartate Receptor Antagonists

The NMDA receptor is a cell-surface protein complex, widely distributed in the mammalian central nervous system that belongs to the class of ionotropic-glutamate receptors. It is involved in excitatory-synaptic transmission and the regulation of neuronal growth. The structure comprises a ligand-gated/voltage-sensitive ion channel. The NMDA receptor is highly complex and is believed to contain at least five distinct binding (activation) sites: a glycine-binding site, a glutamate-binding site (NMDA-binding site); a PCP-binding site, a polyamine-binding site, and a zinc-binding site. In general, a receptor antagonist is a molecule that blocks or reduces the ability of an agonist to activate the receptor. As used herein, an "NMDA-receptor antagonist" means any compound or composition, known or to be discovered, that when contacted with an NMDA receptor in vivo or in vitro, inhibits the flow of ions through the NMDA-receptor ion channel.

An NMDA-receptor antagonist can contain one or more chiral centers and/or double bonds and, therefore, exist as stereoisomers, such as double-bond isomers (i.e., geometric isomers), enantiomers, or diastereomers. As used herein, the term "NMDA-receptor antagonist" encompass all such enantiomers and stereoisomers, that is, both the stereomerically-pure form (e.g., geometrically pure, enantiomerically pure, or diastereomerically pure) and enantiomeric and stereoisomeric mixtures, e.g., racemates. The term "NMDA-receptor antagonist" further encompasses all pharmaceutically acceptable salts, all complexes (e.g., hydrates, solvates, and clathrates), and all prodrugs of NMDA-receptor antagonist.

NMDA-receptor antagonist suitable for use in the invention can be identified by testing NMDA-receptor antagonist for local-anesthetic and peripheral antinociceptive properties according to standard pain models. See e.g., J. Sawynok et al., 82 PAIN 149 (1999); J. Sawynok et al., 80 PAIN 45 (1999).

Preferably, the NMDA-receptor antagonist is a non-competitive NMDA-receptor antagonists, more preferably, ketamine, even more preferably, ketamine hydrochloride.

1. N-methyl-D-aspartate Receptor Antagonists That Block The NMDA Receptor at the Glycine Binding Site As used herein the meaning of the phrase "NMDA-receptor antagonist" encompasses any compound or composition that antagonizes the NMDA receptor by binding at the glycine site. For a review on glycine-site NMDA-receptor antagonists, see LEESON, P. D., GLYCINE SITE N-METHYL-D-ASPARTATE RECEPTOR ANTAGONISTS, Chapter 13 in DRUG DESIGN FOR NEUROSCIENCE, (Kozikowski, A. P. ed. 338–381, 1993). Glycine-site NMDA-receptor antagonists can be identified by standard in vitro and in vivo assays. See, for example, the assays described in U.S. Pat. No. 6,251,903 (issued Jun. 26, 2001); U.S. Pat. No. 6,191,165 (issued Feb. 20, 2001; Grimwood et al. 4 MOLECULAR PHARMACOLOGY 923 (1992); Yoneda et al. 62 J. NEUROCHEM. 102 (1994); and Mayer et al. J. NEUROPHYSIOL. 645 (1988), all of which citations are hereby expressly incorporated herein by reference.

Glycine-site NMDA-receptor antagonists include, but are not limited to, glycinamide, threonine, D-serine, felbamate, 5,7-dichlorokynurenic acid, and 3-amino-1-hydroxy-2-pyrrolidone (HA-966), diethylenetriamine, 1,10-diaminodecane, 1,12-diaminododecane, and ifenprodil and those described in U.S. Pat. Nos. 6,251,903; 5,914,403 (issued Jun. 22, 199); U.S. Pat. No. 5,863,916 (issued Jan. 26, 1999); U.S. Pat. No. 5,783,700 (issued Jul. 21, 1998); and U.S. Pat. No. 5,708,168 (issued Jan. 13, 1998), all of which patents are hereby expressly incorporated herein by reference.

2. N-methyl-D-aspartate Receptor Antagonists That Block the NMDA Receptor at the Glutamate Binding Site As used herein the meaning of the phrase "NMDA-receptor antagonist" encompasses any compound or composition that antagonizes the NMDA receptor by binding at the glutamate site also referred to herein as "competitive NMDA-receptor antagonists"; see, for example, Olney & Farber, 13 NEUROPSYCHOPHARMACOLOGY 335 (1995).

Competitive NMDA antagonists include, but are not limited to, 3-((−)-2-carboxypiperazin-4-ylpropyl-1-phosphate (CPP); 3-(2-carboxypiperzin-4-yl)-prpenyl-1-phosphonate (CPP-ene); 1-(cis-2-carboxypiperidine-4-yl) methyl-1-phosphonic acid (CGS 19755), D-2-Amino-5-phosphonopentanoic acid (AP5); 2-amino-phosphonoheptanoate (AP7); D,L-(E)-2-amino-4-methyl-5-phosphono-3-pentenoic acid carboxyethyl ester (CGP39551); 2-amino-4-methyl-5-phosphono-pent-3-enoic acid (CGP 40116); (4-phosphono-but-2-enylamino)-acetic acid (PD 132477); 2-amino-4-oxo-5-phosphono-pentanoic acid (MDL 100,453); 3-((phosphonylmethyl)-sulfinyl)-D,L-alanine; amino-(4-phosphonomethyl-phenyl)-acetic acid (PD 129635); 2-amino-3-(5-chloro-1-phosphonomethyl-1H-benzoimidazol-2-yl)-propionic acid; 2-amino-3-(3-phosphonomethyl-quinoxalin-2-yl)-propionic acid; 2-amino-3-(5-phosphonomethyl-biphenyl-3-yl)-propionic acid (SDZ EAB 515); 2-amino-3-[2-(2-phosphono-ethyl)-cyclohexyl]-propionic acid (NPC 17742); 4-(3-phosphono-propyl)-piperazine-2-carboxylic acid (D-CPP); 4-(3-phosphono-allyl)-piperazine-2-carboxylic acid (D-CPP-ene); 4-phosphonomethyl-piperidine-2-carboxylic acid (CGS 19755); 3-(2-phosphono-acetyl)-piperidine-2-carboxylic acid (MDL 100,925); 5-phosphono-1,2,3,4-tetrahydro-isoquinoline-3-carboxylic acid (SC 48981); 5-(2-phosphono-ethyl)-1,2,3,4-tetrahydro-isoquinoline-3-carboxylic acid (PD 145950); 6-phosphonomethyl-decahydro-isoquinoline-3-carboxylic acid (LY 274614); 4-(1H-tetrazol-5-ylmethyl)-piperidine-2-carboxylic acid (LY 233053 and 235723); 6-(1H-Tetrazol-5-ylmethyl)-decahydro-isoquinoline-3-carboxylic acid (LY 233536). References that disclose other competitive NMDA-receptor antagonists as well as assays for identifying competitive NMDA-receptor antagonists include Jia-He Li, et al., 38 J. MED. CHEM. 1955 (1995); Steinberg et al., 133 NEUROSCI. LETT. 225 (1991); Meldrum et al., 11 TRENDS PHARMACOL. SCI., 379 (1990); Willetts et al., 11 TRENDS PHARMACOL. SCI. 423 (1990); Faden et al., 13 TRENDS PHARMACOL. SCI. 29 (1992); Rogawski 14 TRENDS PHARMACOL. SCI. 325 (1993); Albers et al., 15 CLINICAL NEUROPHARM. 509 (1992); Wolfe et al., 13 AM. J EMERG. MED., 174 (1995); and Bigge, 45 BIOCHEM. PHARMACOL. 1547 (1993), all of which citations are hereby expressly incorporated herein by reference.

3. N-methyl-D-aspartate Receptor Antagonists that Block the NMDA Receptor at the PCP Binding Site As used herein the meaning of the phrase "NMDA-receptor antagonist" encompasses any compound or composition that antagonizes the NMDA receptor by binding at the PCP (phencyclidine) site, referred to herein as "non-competitive NMDA-receptor antagonists"; see, for example, Bigge 45 BIOCHEM. PHARMACOL. 1547 (1993).

Non-competitive NMDA-receptor antagonists can be identified using routine assays, for example, those described in U.S. Pat. No. 6,251,948 (issued Jun. 26, 2001); U.S. Pat. No. 5,985,586 (issued Nov. 16, 1999), and U.S. Pat. No. 6,025,369 (issued Feb. 15, 2000); Jacobson et al., 110 J. PHARMACOL. EXP. THER. 243 (1987); and Thurkauf et al., 31 J. MED. CHEM. 2257 (1988), all of which citations are hereby expressly incorporated herein by reference.

Examples of non-competitive NMDA-receptor antagonists that bind at the PCP site include, but are not limited to, ketamine, phencyclidine, dextromethorphan, dextrorphan, dexoxadrol, dizocilpine (MK-801), remacemide, thienylcyclohexylpiperidine (TCP), N-allylnometazocine (SKF 10,047), cyclazocine, etoxadrol, (1,2,3,4,9,9a-hexahydro-fluoren-4a-yl)-methyl-amine (PD 137889); (1,3,4,9,10,10a-hexahydro-2H-phenanthren-4a-yl)-methyl-amine (PD 138289); PD 138558, tiletamine, kynurenic acid, 7-chloro-kynurenic acid, and memantine; and quinoxalinediones, such as 6-cyano-7-nitroquinoxaline-2,3-dione (CNQX) and 6,7-dinitro-quinoxaline-2,3-dione (DNQX).

4. N-methyl-D-aspartate Receptor Antagonists that Block the NMDA Receptor at the Polyamine or Zinc Binding Site and other NMDA-receptor Antagonists As used herein the meaning of "NMDA-receptor antagonist" encompasses compounds that block the NMDA receptor at the polyamine binding site, the zinc-binding site, and other NMDA-receptor antagonists that are either not classified herein according to a particular binding site or that block the NMDA receptor by another mechanism. Examples of NMDA-receptor antagonists that bind at the polyamine site include, but are not limited to, spermine, spermidine, putrescine, and arcaine. Examples of assays useful to identify NMDA-receptor antagonists that act at the zinc or polyamine binding site are disclosed in U.S. Pat. No. 5,834,465 (issued Nov. 10, 1998), hereby expressly incorporated by reference herein.

Other NMDA-receptor antagonists include, but are not limited to, amantadine, eliprodil, iamotrigine, riluzole, aptiganel, flupirtine, celfotel, levemopamil, 1-(4-hydroxyphenyl)-2-(4-phenylsulfanyl-piperidin-1-yl)-propan-1-one; 2-[4-(4-fluoro-benzoyl)-piperidin-1-yl]-1-naphthalen-2-yl-ethanone (E 2001); 3-(1,1-dimethyl-heptyl)-9-hydroxymethyl-6,6-dimethyl-6a,7,8,10a-tetrahydro-6H-benzo[c]chromen-1-ol (HU-211); 1-{4-[1-(4-chlorophenyl)-1-methyl-ethyl]-2-methoxy-phenyl}-1H-[1,2,4]triazole-3-carboxylic acid amide (CGP 31358); acetic acid 10-hydroxy-7,9,7',9'-tetramethoxy-3,3'-dimethyl-3,4,3',4'-tetrahydro-1H, 1'H-[5,5']bi[benzo[g]isochromenyl]-4-yl ester (ES 242-1); 14-hydroxy-11-isopropyl-10-methyl-5-octyl-10,13-diaza-tricyclo[6.6.1.04,15]pentadeca-1,4,6,8 (15)-tetraen-12-one; and 4,5-dioxo-4,5-dihydro-1H-benzo[g]indole-2,7,9-tricarboxylic acid (PQQ) and pharmaceutically acceptable salts thereof.

5. Concentration of NMDA-receptor Antagonist in Compositions of the Invention

The amount of NMDA-receptor antagonist in compositions of the invention will vary according to the type and identity of the NMDA-receptor antagonist, the concentration and identity of the antidepressant, and the painful indiction treated. Dosages and concentrations for a particular NMDA-receptor antagonist can be optimized according to routine experiments using well-known pain models, for example, those described in J. Sawynok et al., 82 PAIN 149 (1999) and J. Sawynok et al., 80 PAIN 45 (1999).

In general, the amount of NMDA-receptor antagonist in the compositions of the invention is within the range of from about 0.1 percent to about 5 percent of the total weight of the composition, more preferably, of from about 0.3 percent to about 0.5 percent of the total weight of the composition.

D. The Lipophilic Component

The lipophilic component in the compositions of the invention can be any water-insoluble (hydrophobic) organic material or mixture of materials that can form a stable emulsion comprising an antidepressant and an NMDA-receptor antagonist, suitable for intradermal administration. Preferably, the lipophilic component comprises about 15% to about 40% by weight of the total composition weight, more preferably, about 20% by weight.

Suitable lipophilic components are well known in the art and include, but are not limited to, vegetable, nut, and seed oils, such as almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, crambe oil, wheat germ oil, and cocoa butter; animal oils and fats, such as lanolin, tallow, lard, beef fat, butterfat, mink oil, and fish oils; hydrocarbon and petroleum oils, such as petrolatum, mineral oil, and liquid paraffin; and higher fatty acids such as lauric acid, myristic acid, palmitic acid, stearic acid, behenic acid, oleic acid, 12-hydroxystearic acid, undecylenic acid, tall acid, lanolin fatty acid, isostearic acid, linoleic acid, and linolenic acid. Preferably, the lipophilic component is a petroleum oil, such as petrolatum, mineral oil, or liquid paraffin, more preferably, petrolatum.

Preferably, the lipophilic component further comprises a "stiffening agent" (i.e., a hydrophobic material that is a solid at room temperature but melts within the temperature range of about 40° C. to 80° C.) to provide a creamy feel to the compositions of the invention. The preferred amount of stiffening agent is about 1% to about 10% by weight of the total composition weight. Examples of suitable stiffening agents include, but are not limited to, cetyl alcohol, cetyl esters wax, microcrystalline wax, paraffin, stearyl alcohol, lauryl alcohol, miracle alcohol, cetostearyl alcohol, white wax, yellow wax, bee wax, candelilla wax, cotton wax, carnauba wax, bayberry wax, rice-bran wax. Cetyl alcohol is the preferred stiffening agent.

Preferably, the lipophilic component further comprises a hydrophobic material that facilitates absorption of the antidepressant and the NMDA-receptor antagonist into the skin, referred to herein as a "lipophilic intradermal-penetration enhancer". The preferred amount of lipophilic-intradermal-penetration enhancer is about 1% to about 15% by weight of the total composition weight. Suitable lipophilic intradermal penetration enhancers include isopropyl myristate, glycerol monolaurate, glycerol monooleate, glycerol monolinoleate, isopropyl isostearate, isopropyl linoleate, isopropyl myristate/fatty acid monoglyceride combination, isopropyl myristate/ethanol/L-lactic acid combination, isopropyl palmitate, methyl acetate, methyl caprate, and methyl laurate.

Preferably, the lipophilic phase further comprises a hydrophobic (water-insoluble) surfactant. The preferred amount of hydrophobic surfactant is about 2% to about 8 % by weight of the total composition weight. Hydrophobic surfactants are well known in the art; for example, but not limited to, emulsifying wax, polyoxyethylene acid, polyoxyethylene alcohol, glycerol monostearate, sorbitan tristearate, sorbitan monopalmitate, sorbitan sesquiloleate, and other sorbitan fatty acid esters.

E. The Surfactant System

The compositions of the invention comprise a surfactant to stabilize the emulsion. Surfactants can be cationic, nonionic, anionic, or amphoteric. For an extensive discussion on surfactants and emulsions, see Gillian M. Eccleston, Emulsions in 5 ENCYCLOPEDIA OF PHARMACEUTICAL TECHNOLOGY 137–184 (James C. Swarbrick & James C. Boylan eds. 1988). For use in the invention, the surfactant can be any intradermally-acceptable hydrophilic or hydrophobic material or mixture of materials capable of stabilizing an oil-in-water type emulsion. One of skill in the art will readily choose a suitable surfactant or surfactant mixture based on the hydrophilic-lipophilic balance (HLB) values of the surfactant and the lipophilic component. The preferred amount of surfactant is about 2% to about 15% by weight of the total weight of the composition, more preferably, about 10%.

The phrase "hydrophilic lipophilic balance" or "HLB", as is well known in the art, refers to the numerical value assigned to a surfactant according to the method of Griffin, for the purpose of facilitating surfactant selection prior to emulsion preparation. For a detailed discussion of the HLB system and tables of numerical values see Griffin 1 J. SOC. COSMET. CHEM. 311 (1949); 1 REMINGTON: THE SCIENCE AND PRACTICE OF PHARMACY 286–289 (Alfonso R. Gennaro ed., 19th ed. 1995); TRANSDERMAL AND TOPICAL DRUG DELIVERY SYSTEMS 542–546 (Tapash K. Ghosh et al. eds., 1997), all of which citations are hereby expressly incorporated by reference herein.

While emulsion preparation is essentially a trial and error practice, in general, if an oil-in-water type emulsion is desired, the formulator should begin formulating with a surfactant system having an HLB value within the range of about 8 to 18 (±2). On the other hand, if a water-in-oil type emulsion is desired, the formulator should begin formulating with a surfactant system having an HLB value within the range of 4 to 6 (±2).

Materials commonly used as hydrophobic components in emulsions are assigned a "required HLB value". The required HLB value is the HLB value that a surfactant or surfactant system must have to effectively emulsify a particular material. For example, to prepare a oil-in-water type emulsion of a lipophilic material that has a required HLB value of 10.5, a surfactant system that has an HLB of about 10.5 (±2) should be used.

Suitable surfactants having HLB values between 8–18 (±2) include, but are not limited to, sorbitan monolaurate, glycerol monostearate, PEG 20 sobitan monolaurate, PEG 20 sobitan monopalmitate, PEG 20 sorbitan monostearate, PEG 20 sobitan monooleate, PEG 20 sobitan trioleate, PEG 8 stearate, PEG 40 stearate, PEG-100 stearate, and other PEG stearates; PEG 4 lauryl ether, PEG 21 stearyl ether, PEG 2 oleyl ether.

In addition, mixtures of surfactants are suitable for use in the invention. As a general rule, when mixtures of surfactants are used, the HLB value of the surfactant mixture should be within ±2 to the required HLB value for the lipophilic component (typically between 8 and 18 (±2)). HLB values are algebraically additive making such calculations relatively simple. Suitable surfactant mixtures include, but are not limited to sorbitan tristearate and PEG 20 sorbitan monostearate; sorbitan monopalmitate and PEG 20 sorbitan monopalminate; and sorbitan sesquioleate and PEG 20 laurly ether.

F. Preservatives

In a preferred embodiment, the compositions of the invention further comprise a preservative. In general, topical formulations require preservation from microbial contamination that can effect the stability of the formulation and infect the user. When present in a composition of the invention, the amount of preservative is preferably from about 0.001% to about 1% by weight of the total composition weight, more preferably from about 0.01% to about 0.5% by weight. In some instances, It is also advantageous to include an antioxidant to preserve medicaments and excipients present in topical formulations. Some medicaments and excipients are oxygen labile and can undergo oxidation. When present in a composition of the invention, the amount of antioxidant is preferably from about 0.001% to about 1% by weight of the total composition weight, more preferably from about 0.01% to about 0.5% by weight.

Examples of preservatives include, but are not limited to, quaternary amines, such as quaternium 15, benzalkonium chloride, cetrimide, benzethonium chloride; and imidizolidinyl urea; organic acids, such as sorbic acid, p-hydroxybenzoic acid, and benzoic acid; parabens, such as methyl paraben and propyl paraben; alcohols, such as benzyl alcohol and isopropyl alcohol; phenols, such as triclosan, chlorhexidine, and thimerosal; hydantoin derivatives; chloromethylthiazoline; methylisothiazoline; phenyoxyethol; hexetidine; chlorohexydingluconate; and imidazolidinylurea. Preferably the preservative is methyl paraben, propyl paraben, or a mixture thereof.

Examples of antioxidants include, but are not limited to, ascorbic acid and its esters, sodium bisulfite, sodium metabisulfite, thiourea, butylated hydroxytoluene, butylated hydroxyanisole, tocopherols, alkyl gallates, and chelating agents like EDTA and citric acid.

G. Anti-foaming Agents

In a preferred embodiment, the compositions of the invention further comprise an anti-foaming agent to facilitate manufacture. Anti-foaming agents dissipate foam by destabilizing the air-liquid interface and allow liquid to drain away from air pockets. When present in a composition of the invention, the amount of anti-foaming agent is preferably from about 0.01% to about 1% by weight of the total composition weight, more preferably from about 0.1% to about 0.5% by weight.

Examples of anti-foaming agents include simethicone, dimethicone, ethanol, and ether. Preferably, the anti-foaming agent is simethicone.

H. Emollients, Humectants, and Skin Protectants

In a preferred embodiment, the compositions of the invention further comprise an emollients, a humectants, or a skin protectant, preferably a humectant to soothe and hydrate the skin. When present in a composition of the invention, the amount of humectant, skin protectant, or emollient is preferably from about 1% to about 10% by weight of the total composition weight, more preferably from about 2% to about 5% by weight.

Examples of humectants include, but are not limited to, glycerin, sorbitol, polyethylene glycols, urea, propylene glycol, 1,3-butylene glycol, ethanol, and isopropanol. In a preferred embodiment sorbitol is the humectant, preferably, 70% aqueous sorbitol solution. Examples of emollients include, but are not limited to, cholesterol and glycerol. Examples of skin protectants include, but are not limited to, vitamin E oil, allatoin, glycerin, zinc oxide, vitamins A, B (e.g. biotin and pantothenic acid), C, E, F, H, and P, and esters thereof.

I. Penetration Enhancers

In another embodiment, the compositions of the invention can further comprise a penetration enhancer. When present in a composition of the invention, the amount of penetration enhancer is preferably from about 1% to about 10% by weight of the total composition weight, more preferably from about 2% to about 5% by weight.

Penetration enhancers can be included in the compositions of the invention to optimize transfer of the antidepressant and the NMDA-receptor antagonist through the stratum corneum and into the dermis to provide a local effect. For a discussion of use of penetration enhancers in topical formulations see generally, PERCUTANEOUS PENETRATION ENHANCERS (Eric W. Smith & Howard I. Maibach eds. 1995); Ghosh, T. K. et al. 17 PHARM. TECH. 72 (1993); Ghosh, T. K. et al. 17 PHARM. TECH. 62 (1993);Ghosh, T. K. et al. 17 PHARM. TECH. 68 (1993), all of which citations are hereby incorporated herein by reference. The penetration enhancer should be pharmacologically inert, non-toxic, and non-allergenic, have rapid and reversible onset of action, and be compatible with the compositions of the invention.

Examples of penetration enhancers include, but are not limited to, transcutol P, ethyl alcohol, isopropyl alcohol, lauryl alcohol, salicylic acid, octolyphenylpolyethylene glycol, polyethylene glycol 400, propylene glycol, N-decylmethylsulfoxide, DMSO and the azacyclo compounds, as disclosed in U.S. Pat. Nos. 4,755,535; 4,801,586; 4,808,414; and 4,920,101, all of which patents are hereby expressly incorporated herein by reference. Preferably, the penetration enhancer is transcutol P.

J. Other Local Anesthetics

The compositions of the invention can further comprise one or more additional local anesthetics besides an antidepressant and an NMDA-receptor antagonist. As used herein, the term "local anesthetic" means any compound or composition that provides local numbness or analgesia or any drug that provides a regional blockage of nociceptive pathways (afferent and/or efferent). The local anesthetic can be any local anesthetic known or to be developed. When present in a composition of the invention, the amount of local anesthetic is preferably from about 0.1% to about 10% by weight of the total composition weight.

Examples of local anesthetics suitable for use with the invention include sodium-channel blockers. Sodium-channel blockers, such as lidocaine prevent the generation and conduction of nerve impulses by decreasing or preventing the large transient increase in the permeability of excitable membranes to Na+. Examples of sodium-channel blockers include, but are not limited to, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or pharmaceutically-acceptable salts thereof, or mixtures thereof. Preferred sodium-channel blockers, include lidocaine, procaine, bupivacaine, prilocaine, mepivacaine, etidocaine, ropivacaine, dibucaine, and pharmaceutically-acceptable salts thereof and mixtures thereof. The most preferred local anesthetic is lidocaine and pharmaceutically acceptable salts thereof.

Opioids, such as morphine are known to have local-anesthetic properties when topically administered in mammals. See, for example, U.S. Pat. No. 5,948,389 (issued Sep. 7, 1999) and Christoph Stein & Alexander Yassouridis 71 Pain 119 (1997).

As used herein the term "opioid" means all agonists and antagonists of opioid receptors, such as mu ($\mu$), kappa ($\kappa$), and delta ($\delta$) opioid receptors and subtypes thereof. For a discussion of opioid receptors and subtypes see GOODMAN & GILMAN'S THE PHARMACOLOGICAL BASIS OF THERAPEUTICS 521–525 (Joel G. Hardman et al. eds., 9th ed. 1996), hereby expressly incorporated herein by reference. The opioid can be any opioid receptor agonist or antagonist known or to be developed. Preferred opioids interact with the $\mu$-opioid receptor, the $\kappa$-opioid receptor, or both. Preferably, the opioid is an opioid-receptor agonist.

Examples of suitable opioids include, but are not limited to, alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, normorphine, norpipanone, opium, oxycodone, oxymorphone, papaveretum, papaverine, pentazocine, phenadoxone, henazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, and naltrexone or pharmaceutically-acceptable salts thereof, or mixtures thereof.

Examples of peptide opioids include, but are not limited to, Tyr-Gly-Gly-Phe-Leu ([Leu$^5$]enkephalin), Tyr-Gly-Gly-Phe-Met ([Met$^5$]enkephalin), Tyr-Gly-Gly-Phe-Leu-Arg-Arg-Ile-Arg-Pro-Lys-Leu-Lys-Trp-Asp-Asn-Gln (DynorphinA), Tyr-Gly-Gly-Phe-Leu-Arg-Arg-Gln-Phe-Lys-Val-Val-Thr (Dynorphin B), Tyr-Gly-Gly-Phe-Leu-Arg-Lys-Tyr-Pro-Lys ($\alpha$-Neoendorphin), Tyr-Gly-Gly-Phe-Leu-Arg-Lsy-Tyr-Pro ($\beta$-Neoendorphin), Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu ($\beta_h$-Endorphin), [D-Ala$^2$,MePhe$^4$Gly(ol)$^5$]enkephalin (DAMGO), [D-Pen$^2$,D-Pen$^5$]enkephalin (DPDPE), [D-Ser$^2$, Leu$^5$]enkephalin-Thr$^6$ (DSLET), [D-Ala$^2$,D-Leu$^5$] enkephalin (DADL), D-Phe-Cys-Tyr-D-Trp-Orn-Thr-Pen-Thr-NH$_2$(CTOP), [D-Ala$^2$,N-MePhe$^4$,Met(O)$^5$-ol] enkephalin (FK-33824), Tyr-D-Ala-Phe-Asp-Val-Val-Gly-NH$_2$ ([D-Ala$^2$]Deltorphin 1), Tyr-D-Ala-Phe-Glu-Val-Val-Gly-NH$_2$ ([D-Ala$^2$Glu$^4$]Deltorphin (Deltorphin II)), Tyr-Pro-Phe-Pro-NH$^2$ (Morphiceptin), Tyr-Pro-MePhe-D-Pro-NH$^2$ (PL-017), [D-Ala$^2$,Leu$^5$,Cys$^6$]enkephalin (DALCE) or pharmaceutically-acceptable salts thereof, or mixtures thereof. Preferred opioids include morphine, loperamide, and loperamide derivatives such as those disclosed in U.S. Pat. Nos. 5,763,445; 5,981,513; 5,869,521; 5,744,458; 5,760,023; 5,798,093; 5,849,762; 5,811,078; 6,004,964; 5,962,477; 5,688,955; 5,888,494; 5,646,151; and 5,667,773 or pharmaceutically-acceptable salts thereof, or mixtures thereof, all of which patents are hereby expressly incorporated herein by reference. The most preferred opioid is morphine or a pharmaceutically-acceptable salt thereof.

Other agents with local-anesthetic properties include analgesics, such as non-steroidal anti-inflammatories ("NSAIDs"), see, for example, TRANSDERMAL AND TOPICAL DRUG DELIVERY SYSTEMS 87–93 (Tapash K. Ghosh et al. eds., 1997). Examples of non-narcotic analgesics with local-aesthetic properties include, but are not limited to, acetylsalicylic acid, ketoprofen, piroxicam, diclofenac, indomethacin, and ketorolac.

In yet another embodiment of the current invention, agents may be included in the compositions of the invention to prolong the local-anesthetic effect, such as, a glucocorticosteroid (see, for example, U.S. Pat. No. 5,922,340, incorporated herein by reference) or a vasoconstrictor, such as a catecolamine.

K. Other Excipients

The compositions of the invention can further comprise one or more additional ingredients, such as one or more thickening agents, medicinal agents or pharmaceuticals, bioadhesive polymers, inert carriers, lipid absorbents, viscosity stabilizers, chelating agents, buffers, anti-fading agents, stabilizers, moisture absorbents, fragrances, colorants, film-forming materials, and refatting agents, etc. One of skill in the art will readily be able to choose such additional excipients based on the physical and chemical properties desired in the final topical formulation. Of course, a single excipient may have multiple functions and properties.

1. Thickening Agents

The compositions of the invention can further comprise one or more thickening agents. Thickening agents are used to increase viscosity and improve bioadhesive properties. When present in a composition of the invention, the amount of thickening agent is preferably from about 1% to 10% by weight of the total composition weight, more preferably from about 2% to about 5% by weight.

Examples of thickening agents include, but are not limited to, cellulose, hydroxypropyl cellulose, methyl cellulose, polyethylene glycol, sodium carboxymethyl cellulose, polyethylene oxide, xanthan gum, guar gum, agar, carrageenan gum, gelatin, karaya, pectin, and locust-bean gum, aliginic acid, bentonite carbomer, povidone, and tragacanth.

2. Medicinal Agents

The compositions of the invention can include medicinal agents or their pharmaceutically acceptable salts. One of skill in the art can readily choose a medical agent to incorporate into the compositions of the invention and its appropriate concentration depending on the indication and desired effect. Examples of medicinal agents include, but not limited to, antifungals such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics, such as mupirocin, erthromycin, clindamycin, gentamicin, polymyxin, bacitracin, and silver sulfadiazine; antiseptics, such as iodine, povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride; and anti-inflammatories, such as hydrocortisone, prednisone, triamcilolone, betamethasone, dexamethasone.

3. Bioadhesive Polymers

The compositions of the invention can include one or more bioadhesive polymers. Bioadhesive polymers are also useful in the present invention to hydrate the skin and enhance its permeability. Bioadhesive polymers can also function as thickening agents. Examples of bioadhesive polymers include, but are not limited to, pectin, alginic acid, chitosan, hyaluronic acid, polysorbates, such as polysorbate-20, -21, -40, -60, -61, -65, -80, -81, -85; poly (ethyleneglycol), such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g. aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example, pluronic lethicin organogel (see 1 INTERNATIONAL JOURNAL OF PHARMACEUTICAL COMPOUNDING 71 (1997)); poly(vinyl alcohol); polyacrylamide; hydrolyzed polyacrylamide; poly(vinyl pyrrolidone); poly(methacrylic acid); poly(acrylic acid) or crosslinked polyacrylic acid, such as carbomer, i.e., a homopolymer of acrylic acid crosslinked with either an allyl ether of pentaerythritol, an allyl ether of sucrose, or an allyl ether of propylene (e.g., Acrisint® 400, 410, or 430 commercially available from 3V Inc. Weehawkin, N.J.); Orabase® (i.e., a mixture of gelatine, pectin and sodium carboxymethyl cellulose in a plasticized hydrocarbon gel, commercially available from Hoyt laboratories, Needham, Mass.); Carafate® (sulfated sucrose and aluminum hydroxide, commercially available from Marion Laboratories, Inc., Kansas City, Mo.). The block copolymers of ethylene oxide and propylene oxide are particularly preferred.

L. Methods of Manufacture

The compositions of the invention is prepared according to standard methods, well known in the art, for preparing oil-in-water emulsions for topical administration. For example, the methods recited in 1 REMINGTON: THE SCIENCE AND PRACTICE OF PHARMACY 289 (Alfonso R. Gennaro ed., 19th ed. 1995), hereby expressly incorporated herein by reference, can be used. Also, Example preparations are recited in the Example section below.

For example, the components can be separated into those that are water soluble and those that are oil soluble. The water-soluble components can be mixed together in one vessel to form a solution and the oil-soluble components can be mixed together in a separate vessel and heated (e.g., 70° C. to 80° C.) to form a solution. The two solutions can then be mixed and the mixture allowed to cool. This method requires nothing more than two beakers and a heating apparatus. Homogenation is achieved using a high-shear rate blender or other suitable apparatus. The appropriate droplet size is achieved by standard adjustment of the shear rate during high-speed mixing followed by droplet size analysis as described in 1 REMINGTON: THE SCIENCE AND PRACTICE OF PHARMACY 282–283 (Alfonso R. Gennaro ed., 19th ed. 1995) and Allen & Terence, PARTICLE SIZE MEASUREMENT 483 (4th ed. 1990, both or which citations are hereby expressly incorporated herein by reference. Suitable equipment and methods for preparing emulsions and compositions of the invention, such as high-shear rate blenders are described in 2 REMINGTON: THE SCIENCE AND PRACTICE OF PHARMACY 1509–1515 (Alfonso R. Gennaro ed., 19th ed. 1995), hereby expressly incorporated herein by reference. Methods for preparation of emulsions for topical administration, suitable for preparing compositions of the invention, are also described in Bernard Idson, *Pharmaceutical Emulsions* in 1 PHARMACEUTICAL DOSAGE FORMS: DISPERSE SYSTEMS 199 (Herbert A. Lieberman et al. eds. 1988), hereby expressly incorporated herein by reference.

The compositions of the invention are then packaged and stored according to well-known methods. For example, see the packaging procedures described in 1 REMINGTON: THE SCIENCE AND PRACTICE OF PHARMACY 390–391 (Alfonso R. Gennaro ed., 19th ed. 1995), hereby incorporated herein by reference. If desired, the compositions of the invention can be sterilized according to well-known methods, for example, the methods described in 2 REMINGTON: THE SCIENCE AND PRACTICE OF PHARMACY 1463–1486 (Alfonso R. Gennaro ed., 19th ed. 1995), hereby incorporated herein by reference.

M. Methods of Administration

1. Topical Application

The compositions of the invention can be topically administered to intact skin by a medical professional or by the patient by simple mechanical rubbing into the application site. In applying these compositions to the skin, for maximum effectiveness and increased absorption, the area to which the composition is to be administered is first cleansed with an astringent, such as a standard commercial antiseptic or alcohol. The area is then allowed to dry for a few seconds. Next, the composition of the invention is rubbed on to the complete target area of the skin (the painful area) and gently, but firmly, massaged in with the fingertips until all visible gel or cream has been absorbed.

After application of a composition of the invention, the application site can be covered with a dressing. The term "dressing", as used herein, means a covering designed to protect a previously applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the pain site, which provides for greater comfort. In another embodiment, a composition of the invention can be incorporated into a dressing, which dressing is then applied to the skin or painful area.

2. Administration via an Intradermal Patch

In one embodiment of the current invention, the compositions of the invention are contained in a patch that is applied adjacent to the area of skin to be treated. As used herein a "patch" comprises at least a composition of the invention and a covering layer, such that, the patch can be placed over the area of skin to be treated. Preferably, the patch is designed to maximize drug delivery through the stratum corneum and into the epidermis or dermis, and to minimize absorption into the circulatory system, reduce lag time, promote uniform absorption, and reduce mechanical rub-off.

Preferably, the patch components resemble the viscoelastic properties of the skin and conform to the skin during movement to prevent undue shear and delamination.

Patches comprising the compositions of the invention have advantages over conventional methods of administration. One advantage is that the dose is controlled by the patch's surface area. Other advantages of patches are constant rate of administration, longer duration of action (the ability of to adhere to the skin for 1, 3, 7 days or longer); improved patient compliance, non-invasive dosing, and reversible action (i.e., the patch can simply be removed).

Examples of patches suitable for use with compositions of the invention include (1) the matrix-type patch; (2) the reservoir-type patch; (3) the multi-laminate drug-in-adhesive type patch; (4) the monolithic drug-in-adhesive type patch; and (5) hydrogel patch; see generally Ghosh, T. K.; Pfister, W. R.; Yum, S. I. *Transdermal and Topical Drug Delivery Systems,* Interpharm Press, Inc. p. 249–297, hereby expressly incorporated herein by reference). These patches are well known in the art and available commercially.

In one embodiment, a composition of the invention is contained in a reservoir-type patch. The reservoir-type patch is characterized by a backing film coated with an adhesive and a reservoir compartment comprising a composition of the invention (see, for example, U.S. Pat. No. 4,615,699, hereby expressly incorporated herein by reference. The adhesive coated backing layer extends around the reservoir's boundaries to provide a concentric seal with the skin and hold the reservoir adjacent to the skin.

In one embodiment, a composition of the invention is contained in a drug-in-adhesive or hydrogel patch. The monolithic drug-in-adhesive patch design is characterized by the inclusion of the drug formulation in the skin contacting adhesive layer, a backing film and preferably, a release liner. The adhesive functions both to release the anesthetic and adhere the anesthetic matrix to the skin. The drug-in-adhesive system does not require an adhesive overlay and thus the patch size is minimized. Also, drug-in-adhesive type patches are thin and comfortable (e.g., U.S. Pat. No. 4,751,087, hereby incorporated herein by reference).

The multi-laminate drug-in-adhesive patch design further incorporates additional semi-permeable membrane between two distinct drug-in-adhesive layers or multiple drug-in-adhesive layers under a single backing film (Peterson, T. A. and Dreyer, S. J. Proceed. *Intern. Symp. Control Rel. Bioact. Mater.* 21: 477–478, incorporated herein by reference).

Semi permeable membranes, useful with the reservoir or multi-laminate patch, include thin non-porous ethylene vinyl acetate films or thin microporous films of polyethylene employed in microlaminate solid state reservoir patches.

Adhesives for use with the drug-in-adhesive type patches are well known in the art and selection is readily accomplished by an ordinary practitioner. Three basic types commonly used are polyisobutylenes, silicones, acrylics, and hydrogels. Adhesives useful in the present invention can function under a wide range of conditions, such as, high and low humidity, bathing, sweating etc. Preferably the adhesive is a composition based on natural or synthetic rubber, polyacrylate, polyvinylacetate, polybutylacrylate, polymethylacrylate, polydimethylsiloxane, and hydrogels (e.g., high molecular weight polyvinylpyrrolidone, oligomeric polyethylene oxide, or a mixture thereof). The most preferred is polyacrylate and hydrogels. The most preferred adhesives are hydrogels and polyacrylates. In one a embodiment, the hydrogel is electron-beam cross-linked polyvinylpyrrolidone ("PVP") where the PVP is of an average molecular weight of about 500,000 Daltons to about 2,000,000 Daltons, preferably, about 900,000 Daltons to about 1,500,000 Daltons. Exemplary PVP-hydrogels for use in the invention are described in WO 93/10163 (published May 27, 1993) page 12, line 24 through page 13, line 3; U.S. Pat. No. 4,989,607 column 13, lines 10–25; EP 0 107 376 (published Feb. 5, 1984) page 19, lines 10–30; D. Darwis 42 RADIAT. PHYS. CHEM. 907 (1993); and Olgun Guven & Murat Sen 32 POLYMER 2491 (1991), all of which citations are hereby expressly incorporated herein by reference.

Suitable release liners include but are not limited to occlusive, opaque, or clear polyester films with a thin coating of pressure sensitive release liner (e.g., silicone-fluorsilicone, and perfluorcarbon based polymers.

Backing films may be occlusive or permeable and are derived from synthetic polymers like polyolefin oils polyester, polyethylene, polyvinylidine chloride, and polyurethane or from natural materials like cotton, wool, etc. Occlusive backing films, such as synthetic polyesters, result in hydration of the outer layers of the stratum corneum while non-occlusive backings allow the area to breath (i.e., promote water vapor transmission from the skin surface). More preferably the backing film is an occlusive polyolefin foil (Alevo, Dreieich, Germany). The polyolefin foil is preferably about 0.6 to about 1 mm thick.

In general, the composition of the invention will comprise from about 0.5 percent to about 40 percent by weight of the patch, preferably from about 10 percent to about 30 percent, more preferably from about 15 percent to about 25 percent, and most preferably from about 18 percent to about 22 percent by weight of the patch.

The Patches for use with compositions of the invention can be manufactured, packaged, stored and labeled according to standard procedures. For example, see the procedures described in Bova et al., *Product Development and Technology Transfer for Transdermal Therapeutic Systems* in TRANSDERMAL CONTROLLED SYSTEMIC MEDICATIONS 379–396 (Y. W. Chien ed. 1987); J. W. Dohner, *Development of Processes and Equipment for Rate Controlled Transdermal Therapeutic Systems* in TRANSDERMAL CONTROLLED SYSTEMIC MEDICATIONS 349–364 (Y. W. Chien ed. 1987); H-M Wolf et al., *Development of Processes and Technology for Adhesive-Type Transdermal Therapeutic Systems* in TRANSDERMAL CONTROLLED SYSTEMIC MEDICATIONS 365–378 (Y. W. Chien ed. 1987), all of which citations are hereby incorporated herein by reference.

3. Dosage

Selection of the appropriate dosage for the application site is an important consideration. The rate of intradermal anesthetic administration from the topical formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum; see R. C. Wester. & H. I. Maibach *Regional variation in Percutaneous Absorption* in PERCUTANEOUS ABSORPTION, MECHANISM, METHODOLOGY, DRUG DELIVERY 111–119 (R. L. Bronaugh & H. I. Maibach eds., 2nd ed. 1989), hereby expressly incorporated herein by reference. Of course, the dosages and dosing frequency will be determined by a trained medical professional and will depend upon many factors such as application site and size and the severity of the indication.

With gels, creams, or ointments, typically 1 to 4 applications are required per day. Generally, about 0.5 g/cm$^2$ of skin area to about 5 g/cm$^2$, preferably 1 g/cm$^2$ to about 2 g/cm$^2$ of a composition of the invention is administered to and around the application site. After administration, if desired, the area can be covered with a dressing.

When a patch is used to administer a composition of the invention, the dosage to achieve pain relief is determined by the active surface area of the medicated portion of the patch in direct contact with the skin. Several dosage strengths are advantageous depending upon the severity of the wound. In general, a physician can begin dosing with a low or intermediate strength patch and then, depending upon the effectiveness, adjust the dosage up or down by prescribing a patch of higher or lower active concentration or a patch of larger or smaller surface area, or, in some cases, multiple patches. In general, the composition of the invention will comprise from about 0.5 percent to about 20 percent by weight of the patch, preferably from about 5 percent to about 25 percent by weight of the patch. For matrix (drug-in-adhesive) type patches, the compositions of the invention will comprise from about 0.5 percent to about 20 percent by weight of the patch. For patches comprising a hydrogel, the compositions of the invention will comprise from about 0.5 percent to about 10 percent by weight of the patch. Fresh patches may be administered multiple times per day, but, preferably, a fresh patch is administered about every 18 to about every 48 hours, more preferably daily.

The present invention and its many attendant advantages will be understood from the foregoing description and it will be apparent that various changes in form, construction and arrangement of the parts thereof may be made without departing from the spirit and scope of the invention or sacrificing all of its material advantages, the form hereinbefore described are merely exemplary embodiments thereof.

VI. EXAMPLES

All reagents used in the Examples below are commercially available from standard sources, for example from, Spectrum Laboratory Products, Inc. Gardena, Calif. Amitriptyline hydrochloride was purchased from Spectrum Laboratory Products, Inc. Ketamine hydrochloride was purchased from Medisca, Inc., Plattsburg, N.Y. As used throughout the Examples, "high-strength compositions" refer to compositions comprising about 2% ketamine and about 4% amitriptyline, and "low-strength compositions" refer to compositions comprising about 0.5% ketamine and about 1% amitriptyline.

Example 1

Compositions A and B of the Invention Comprising Amitriptyline and Ketamine

Compositions A and B are compositions according to the invention. The topical amitriptyline-ketamine cream compositions A and B comprising amitriptyline hydrochloride and ketamine hydrochloride were formulated according to the following procedure using the component weights listed in Table 1. The oil-phase components are detailed in Table 2.

TABLE 1

Compositions A and B: High- and Low-strength Ketamine-Amitriptyline Compositions of the Invention

| component | Compositions A (high strength) | | Composition B (low strength) | |
| --- | --- | --- | --- | --- |
| | weight | weight % | weight | weight % |
| ketamine hyrochloride | 138 g | 2.3% | 34.8 g | 0.58% |
| amitriptyline hydrochloride | 270 g | 4.5% | 67.8 g | 1.13% |
| methyl paraben | 12 g | 0.2% | 12 g | 0.2% |
| propyl paraben | 1.2 g | 0.02% | 1.2 g | 0.02% |
| sorbitol (70% solution) | 426 g | 7.1% | 426 g | 7.1% |
| PEG-100 stearate | 390 g | 6.5% | 390 g | 6.5% |
| simethicone | 6 g | 0.1% | 6 g | 0.1% |
| Oil Phase* | 1200 g | 20% | 1200 g | 20% |
| water | 3558 | 59.3% | 3864 | 64.4% |

*Composition of the oil phase is shown in Table 2.

TABLE 2

The Oil-Phase Components of Compositions A and B in Table 1 Above

| component | weight | weight % |
| --- | --- | --- |
| cetyl alcohol | 156 g | 13% |
| isopropyl myristate | 528 g | 44% |
| glycerol stearate | 264 g | 22% |
| petrolatum | 252 g | 21% |

Aqueous-Phase Solution: Sorbitol solution, water, and PEG-100 stearate, were added to a Groen kettle (Model "TDB/8-20 CFC", Groen Division, Dover Corporation, Elk Grove Village, Ill.). The kettle has a self-contained water jacket. The temperature was maintained within the range of about 70° C. to about 80° C. The kettle was covered, and the mixture was heated and stirred. When a solution resulted, the methylparaben, ketamine hydrochloride, and amitriptyline hydrochloride were added. Stirring and heating continued until all ingredients were dissolved.

Oil-Phase Solution: The cetyl alcohol, isopropyl myristate, glycerol stearate and petrolatum were added to a stainless-steel container immersed in a hot water bath. The water-bath temperature was maintained in the range of 70° C. to 80° C. using a hot-plate. The solution was heated and stirred (Lab-Stirrer, Model LR 400 C, Fisher Scientific Inc., Pittsburgh, Pa.) until a homogenous liquid resulted. Propylparaben was then added and stirring and heating continued until the propylparaben was completely dissolved.

The oil phase (70° C.) was slowly poured into the aqueous phase (70° C.) and the resulting mixture was stirred for 10 minutes using the kettle-stirring device. The kettle-stirring device was then disassembled and the mixture was emulsified using a high-shear homogenizer (PowerGen Homogenizer, Model 700D, Fisher Scientific Inc., Pittsburgh, Pa.) for 15 minutes. The kettle stirring device was then reassembled to stir the resulting emulsion while the hot water in the kettle jacket was replaced with ice water to cool the emulsion. After the emulsion temperature dropped below 40° C., simethicone was added and the emulsion was then mixed for another 15 minutes using the kettle-stirring device. A Grisona MA filling machine (NAG Nähma AG, Unterägeri, Austria) was used to fill the emulsion into 60 gram aluminum tubes (Peerless Tube Company, Bloomfield, N.J.).

The oil-phase-droplet diameters (weight mean diameter) were measured via laser-light diffraction (Malvern Mastersizer S Laser Diffractor, Malvern Instruments Ltd, Malvern, UK). Prior to the analysis, emulsion samples were dispersed in a 6.5% solution of PEG-100 stearate in purified water. Sample refractive index and carrier-fluid refractive index were set at 1.5295 and 1.33, respectively. The default setting for the Presentation and Analysis Model was "0HD" and "Polydisperse". Droplet size was determined to be in the range of 0.2 microns to 100 microns, the mean-droplet size was 0.34 microns.

Example 2

Compositions C and D of the Invention Comprising Amitriptyline and Ketamine and Transcutol-P as a Permeation Enhancer The procedure described above in Example 1 above was used to prepare amitriptyline-ketamine emulsion compositions C and D, which further contained the permeation enhancer Transcutol-P (ethoxydiglycol, commercially available, for example, from Gattefosse, Westwood, N.J.). Transcutol-P was blended together with water, sorbitol solution, and PEG-100 stearate during formulation of the aqueous phase.

TABLE 3

Compositions C and D: High- and Low-Strength Ketamine-Amitriptyline Compositions of the Invention Comprising a Permeation Enhancer (Transcutol-P)

| component | Compositions C (high strength) | | Composition D (low strength) | |
|---|---|---|---|---|
| | weight | weight % | weight | weight % |
| ketamine hydrochloride | 138 g | 2.3% | 34.8 g | 0.58% |
| amitriptyline hydrochloride | 270 g | 4.5% | 67.8 g | 1.13% |
| methyl paraben | 12 g | 0.2% | 12 g | 0.2% |
| propyl paraben | 1.2 g | 0.02% | 1.2 g | 0.02% |
| transcutol-P | 300 g | 5% | 300 g | 5 |
| sorbitol (70% solution) | 426 g | 7.1% | 426 g | 7.1% |

TABLE 3-continued

Compositions C and D: High- and Low-Strength Ketamine-Amitriptyline Compositions of the Invention Comprising a Permeation Enhancer (Transcutol-P)

| component | Compositions C (high strength) | | Composition D (low strength) | |
|---|---|---|---|---|
| | weight | weight % | weight | weight % |
| PEG-100 stearate | 390 g | 6.5% | 390 g | 6.5% |
| simethicone | 6 g | 0.1% | 6 g | 0.1% |
| Oil Phase* | 1200 g | 20% | 1200 g | 20% |
| water | 3258 g | 54.3% | 3564 g | 59.4% |

*Composition of the oil phase is shown in Table 2 of Example 1 above.

Example 3

Topical Pluronic-gel Formulations E and F Comprising Amitriptyline and Ketamine with a Permeation Enhancer (Transcutol-P)

Topical pluronic gel compositions E and F were prepared for skin-permeation rate comparison to compositions of the invention A–D. The formulation and component weights of compositions E and F are shown in Table 4.

Amitriptyline hydrochloride and ketamine hydrochloride were dissolved in the water in a glass beaker. Methylparaben and propylparaben were mixed with Transcutol-P in a separate beaker. The Transcutol-P solution containing the methylparaben and propylparaben was poured into the amitriptyline hydrochloride/ketamine hydrochloride solution. A glass beaker containing the above solution was then placed inside a ice bath to cool the solution to approximately 5° C. Pluronic F127 was added to the solution with continuous mixing (Lab-Stirrer, Model LR 400 C, Fisher Scientific Inc., Pittsburgh, Pa.) for approximately 12 hours until a clear solution resulted. While maintaining the temperature just below about 10° C., the clear solution was filled into aluminum tubes. When the solution temperature equilibrated to room temperature, it transformed into a clear gel.

TABLE 4

Compositions E and F: High- and Low-Strength Pluronic-Gel Formulations Comprising Amitriptyline and Ketamine with a Permeation Enhancer

| component | Compositions E (high strength gel formulation) | | Composition F (low strength Gel formulation) | |
|---|---|---|---|---|
| | weight | weight % | weight | weight % |
| Amitriptyline HCl | 4.5 | 4.5% | 1.13 | 1.13% |
| Ketamine HCl | 2.3 | 2.3% | 0.58 | 0.58% |
| Methylparaben | 0.2 | 0.2% | 0.2 | 0.2% |
| Propylparaben | 0.02 | 0.02% | 0.02 | 0.02% |
| Transcutol-P | 2.0 | 2.0% | 2.0 | 2.0% |
| Pluronic F127 | 30.0 | 30.0% | 30.0 | 30.0% |
| Water | 61.0 | 61% | 66.1 | 66.1% |

Example 4

Topical Pluronic-Lecithin Gel Formulations G and H Comprising Amitriptyline and Ketamine with a Permeation Enhancer (Transcutol-P)

Pluronic-lecithin-gel (PLO) compositions G and H, which further contained the permeation enhancer transcutol-P, were prepared for skin-permeation rate comparison to compositions of the invention A–D. The formulation and component weights of compositions G and H are shown in Table 5 below.

The indicated amounts of amitriptyline hydrochloride, transcutol-P, ketamine hydrochloride, and pluronic solution were placed into a 200 ml glass beaker and maintained at approximately 5° C. using an ice bath and stirred using a mechanical mixer (Lab-Stirrer, Model LR 400 C, Fisher Scientific Inc., Pittsburgh, Pa.) until a solution resulted.

Methylparaben, propylparaben, vitamin E, lecithin, and isopropyl myristate were mixed in a separate vessel using a glass mortar & pestle via trituration until a solution resulted. The two solutions were combined in the glass mortar and mixed under vigorous trituration for approximately 5 minutes. The finished product was a smooth gel with a yellow tinge.

TABLE 5

Compositions G and H: Pluronic-Lecithin Gel Formulations Comprising Amitriptyline and Ketamine with a Permeation Enhancer (Tanscutol-P)

| component | Composition G (high strength gel formulation) weight | weight % | Composition H (low strength Gel formulation) weight | weight % |
|---|---|---|---|---|
| Amitriptyline HCl | 4.5 | 4.5% | 1.13 | 1.13% |
| Ketamine HCl | 2.3 | 2.3% | 0.58 | 0.58% |
| Methylparaben | 0.2 | 0.2% | 0.2 | 0.2% |
| Propylparaben | 0.02 | 0.02% | 0.02 | 0.02% |
| Transcutol-P | 10 | 10% | 10 | 10% |
| 20% pluronic gel (20% pluronic F127 and 80% water) | 62.98 | 62.98% | 68.07 | 68.07% |
| Vitamin E | 0.2 | 0.2% | 0.2 | 0.2% |
| Lecithin | 9.9 | 9.9% | 9.9 | 9.9% |
| Isopropyl myristate | 9.9 | 9.9% | 9.9 | 9.9% |

Example 5

In Vitro Permeation Through Human Cadaver Skin of Ketamine-amitriptyline Cream and Gel Formulations (Compositions A–J)

A system employing six improved Franz diffusion cells with a diffusional area of 1.767 cm$^2$ (FDC-400, Crown Glass Company, Somerville, N.J.) was used for the permeation studies. The receptor-phase volume was 13 ml and the receptor temperature was maintained at 37 ±0.5° C. with a water jacket. PEG 400/Water (40/60) was used as receptor medium. Human cadaver skin dermatomed at 375 $\mu$m (New York Firefighters Skin Bank, New York, N.Y.) was hydrated at room temperature in normal saline solution for 15 minutes. The skin sample was mounted between the donor and receptor compartments of the cell and clamped with the dermal side in contact with the receptor medium. About 150 mg of compositions A–J were applied to the stratum corneum side. Samples of the receptor fluid (1 ml) were withdrawn at 2, 4, 6, 8, and 24 hours and replaced with the same volume of receptor medium after each sample was taken. The experiment for each formulation was conducted in replicates (n=3). The samples were analyzed for ketamine and amitriptyline concentrations by HPLC assay procedure described below. A cumulative amount of ketamine and amitriptyline permeated per unit surface area of the skin was plotted against time and the permeation rate (flux=$\mu$g/cm$^2$/hr) was determined for ketamine and amitriptyline.

HPLC was performed using a Platinum EPS column © 18, 100 A, 5u, 150×4.6 mm, Part No. 32214, Alltech Associates, Inc., Deerfield, Ill.) using commercially available HPLC apparatus. Mobile phase A was 10/90 (v/v) Acetonitrile/40 mM potassium phosphate buffer (pH 2.5) with 10 mM heptanesulfonic acid sodium salt as ion paring agent. Mobile phase B was 50/50 (v/v) acetonitrile/40 mM potassium phosphate buffer (pH 2.5) with 10 mM heptanesulfonic acid sodium salt as ion paring agent. The gradient program was such that at 0 minutes, a solution of 70% A and 30% B was used; at 10 minutes, 100% B; at 17 minutes, 100% B; at 18 minutes, 70% A and 30% B; at 22 minutes, 70 % A and 30% B. The flow rate was 1.0 ml per minute; column temperature 40° C.; sample temperature at room temperature; injection volume of 25 $\mu$l; wavelength 260 nm; back pressure was approximately 40 kg/cm$^2$. For a run time of 22 minutes, under the above conditions, retention times were as follows: methylparaben, 5.3 minutes; ketamine hydrochloride, 7.6 minutes; propylparaben, 10.3 minutes; amitriptyline hydrochloride, 14.5 minutes.

TABLE 6

Ketamine Permeation Data through Human Cadaver Skin

| Formula No. | Formula type | Strength | permeation rate ($\mu$g/cm$^2$/hr) |
|---|---|---|---|
| A | Composition of the invention | High | 8.64 |
| B | Composition of the invention | Low | 4.09 |
| C | Composition of the invention with Permeation Enhancer | High | 4.77 |
| D | Composition of the invention with Permeation Enhancer | Low | 4.09 |
| E | Pluronic Gel with Permeation Enhancer | High | 1.82 |
| F | Pluronic Gel with Permeation Enhancer | Low | 1.14 |
| G | PLO Gel with Permeation Enhancer | High | 4.55 |
| H | PLO Gel with Permeation Enhancer | Low | 1.36 |

TABLE 7

Amitriptyline Permeation Rate through Human Cadaver Skin

| Formula No. | Formula type | Strength | permeation rate ($\mu$g/cm$^2$/hr) |
|---|---|---|---|
| A | Composition of the invention | High | 2.82 |
| B | Composition of the invention | Low | 2.41 |
| C | Composition of the invention with Permeation Enhancer | High | 1.82 |
| D | Composition of the invention with Permeation Enhancer | Low | 1.86 |
| E | Pluronic Gel with Permeation Enhancer | High | 0.23 |
| F | Pluronic Gel with Permeation Enhancer | Low | 0.14 |
| G | PLO Gel with Permeation Enhancer | High | 0.68 |
| H | PLO Gel with Permeation Enhancer | Low | 0.14 |

Compositions A–D, representative compositions of the invention, provide enhanced permeation rates of ketamine and amitriptyline compared to standard topical formulations E–H. The effect is more pronounced at low-strength concentrations.

Example 6

Chemical and Physical Stability Studies

Physical and chemical stability of composition A, a representative composition of the invention, was evaluated and compared according to International Conference on Harmonisation (ICH) guidelines for Stability Testing of New Drug Substances and Products (Recommended for Adoption at Step 4 of the ICH Process on Oct. 27, 1993 by the ICH Steering Committee), hereby expressly incorporated herein by reference. Samples of compositions of the invention were maintained in storage chambers under controlled temperature and relative humidity ("RH") using a Stability oven, Model No. ES2000, Environmental Specialties, Inc., Raleigh, N.C. Three different storage conditions, 25° C./60% RH, 30° C./60% RH, and 40° C./75% RH, were used in the study. At one and two months, aliquots were removed, and amitriptyline, ketamine, methyl paraben, and propyl paraben were extracted with methanol. The extracts were analyzed by HPLC to determine the percentage of amitriptyline, ketamine, methyl paraben, and propyl paraben remaining in the compositions and thereby determine whether the compositions had lost activity through decomposition or otherwise. The extraction and HPLC analysis was conducted as follows.

One gram of the compositions of the invention or the gels to which they were compared was placed in a glass beaker. For low strength samples, approximately 30 ml of methanol was added as the extraction solvent. The sample was stirred in a hot water bath at 70±100° C. for five (5) minutes, then sonicated in hot tap water (60±10° C.) for five (5) minutes. Ten ml of methanol was added to replace that which evaporated, and the sample was stirred and sonicated as described above. The beaker was then removed from the water bath and stirred while allowed to cool to room temperature. Then the sample was transferred to a volumetric flask. The beaker was rinsed with methanol and the rinsing solvent added to a volumetric flask and methanol was added up to 50 ml. For high-strength samples, the same procedure was used except approximately four times the amount of methanol was used in the extraction. The sample was then filtered through a 0.2 μm PTFE syringe filter. The first 2 ml of filtrate was discarded and the remaining was transferred to an HPLC vial.

The amounts of amitriptyline, ketamine, methylparaben, and propylparaben in the extraction solvent were then determined using high-pressure liquid chromatography. Chemical stability of both the actives and preservatives in emulsion composition A (prepared according to Example 1) is presented in Table 8 as the percentage of actives remaining. This value can be compared to the percentage of actives calculated before storage according to the HPLC method.

The above stability testing shows that composition A, a representative composition of the invention, is chemically stable under the storage conditions for at least two months even at elevated temperatures. Thus, the compositions of the invention show excellent chemical stability.

After storage of the samples under the above conditions, samples were evaluated for physical stability by measuring viscosity and oil-phase droplet size. A Brookhaven™ viscometer (Model RVT, Helipath stand setting, Brookhaven Engineering laboratories, Inc., Middleboro, Mass.) was used to analyze the viscosity of composition A. A T spindle was used at a 5 rpm rotation speed. The sample temperature was maintained at 25° C. during the analysis. The effect of storage on the emulsion viscosity is seen in Table 9.

The oil-phase droplet diameters ("D" weight mean diameter) was measured via laser-light diffraction (Malvern Mastersizer S Laser Diffractor, Malvern Instruments Ltd., Malvern, UK). Prior to the analysis, emulsion samples were dispersed in the 6.5% solution of PEG-100 stearate in purified water. Sample refractive index and carrier fluid refractive index were set at 1.5295 and 1.33 respectively. Default setting for the Presentation and Analysis Model was "OHD" and "Polydisperse". The effect of storage on the droplet size distribution is seen in Table 9.

When the same experiment was conducted with pluronic-lecithin gels G and H, the samples turned yellow and phase separation occurred during storage indicating physical and chemical instability.

TABLE 9

Physical Stability of Composition A following Stability Storage

|  | Initial | Two months | |
| --- | --- | --- | --- |
|  |  | 25° C. | 30° C. |
| Viscosity (cps) | 54,000 | 66,000 | 54,000 |
| D10 (μm) | 0.25 | 0.25 | N/A |
| D50 (μm) | 0.34 | 0.34 | N/A |
| D90 (μm) | 0.47 | 0.48 | N/A |

The data in Table 9 shows that after two months under the storage conditions, composition A, a representative composition of the invention, showed minimal change in the viscosity and internal droplet size. Thus, the compositions of the invention show excellent physical stability.

TABLE 8

Percentage of Actives Remaining in Composition A After Exposure to Stability Testing Conditions

|  | calculated initial | calc. percentage of actives after storage for one month | | | calc. percentage of actives after storage for two months | | |
| --- | --- | --- | --- | --- | --- | --- | --- |
|  | percentage of actives | 25° C. | 30° C. | 40° C. | 25° C. | 30° C. | 40° C. |
| Methylparaben | 104.4% | 103% | 102% | 102% | 101% | 102% | 102% |
| Propylparaben | 101.8% | 102% | 102% | 102% | 102% | 103% | 103% |
| Amitriptyline Hydrochloride | 102.5% | 103% | 102% | 103% | 101% | 102% | 102% |
| Ketamine Hydrochloride | 100.4% | 103% | 102% | 103% | 100% | 100% | 102% |

Example 7

Other Compositions of the Invention

Using the procedure of Example 1, a composition of the invention (composition I) having the following composition was prepared. Brij 721, stearyl alcohol, and light mineral oil comprised the oil phase.

TABLE 10

| | Compositions I | |
|---|---|---|
| component | weight | weight % |
| ketamine hydrochloride | 2.3 g | 2.3% |
| amitriptyline hydrochloride | 4.5 g | 4.5% |
| methyl paraben | 0.2 g | 0.2% |
| Brij 721 | 5 g | 5% |
| stearyl alcohol | 5 g | 5% |
| light mineral oil | 15 g | 15% |
| Brij 72 | 5 g | 5% |
| water | 63 g | 63% |

The present invention is not to be limited in scope by the specific embodiments disclosed in the examples, which are intended as illustrations of a few aspects of the invention, and any embodiments that are functionally equivalent are within the scope of this invention. Indeed, various modifications of the invention in addition to those shown and described herein will become apparent to those skilled in the art and are intended to fall within the scope of the appended claims.

All cited references are hereby incorporated herein in their entireties by reference.

What is claimed is:

1. A emulsion comprising:
   (a) amitriptyline or a pharmaceutically acceptable salt thereof;
   (b) ketamine or a pharmaceutically acceptable salt thereof;
   (c) a lipophilic component;
   (d) water; and
   (e) a surfactant, wherein the emulsion is an oil in water emulsion and further comprises a lipophilic intradermal penetration enhancer selected from the group consisting of isopropyl myristate, glycerol monolaurate, glycerol monooleate, glycerol monolinoleate, isopropyl isostearate, isopropyl linoleate, isopropyl myristate/fatty acid monoglyceride combination, isopropyl myristate/ethanol/l-lactic acid combination, isopropyl palmitate, methyl acetate, methyl caprate, and methyl laurate.

2. The emulsion of claim 1, wherein the mean oil droplet size is within the range of about 0.01 microns to about 100 microns.

3. The emulsion of claim 1, wherein the mean oil droplet size is within the range of about 0.1 microns to about 10 microns.

4. The emulsion of claim 1, wherein an amount of the amitriptyline is within the range of about 0.1% by weight to about 10% by weight of a total weight of the emulsion.

5. The emulsion of claim 1, wherein an amount of ketamine is within the range of about 0.1% by weight to about 10% by weight of a total weight of the emulsion.

6. The emulsion of claim 1, wherein the lipophilic component comprises petrolatum.

7. The emulsion of claim 1, wherein the lipophilic component comprises a stiffening agent.

8. The emulsion of claim 7, wherein the stiffening agent is cetyl alcohol.

9. The emulsion of claim 1 further comprising a humectant or an anti-foaming agent.

* * * * *